United States Patent
Masic et al.

(10) Patent No.: US 11,638,796 B2
(45) Date of Patent: *May 2, 2023

(54) METHODS AND SYSTEMS FOR EXHALATION CONTROL AND TRAJECTORY OPTIMIZATION

(71) Applicant: Covidien LP, Mansfield, MA (US)

(72) Inventors: Milenko Masic, San Diego, CA (US); Peter Doyle, Vista, CA (US); Gardner Kimm, Carlsbad, CA (US)

(73) Assignee: Covidien LP, Mansfield, MA (US)

( * ) Notice: Subject to any disclaimer, the term of this patent is extended or adjusted under 35 U.S.C. 154(b) by 372 days.

This patent is subject to a terminal disclaimer.

(21) Appl. No.: 17/077,196

(22) Filed: Oct. 22, 2020

(65) Prior Publication Data

US 2021/0085900 A1 Mar. 25, 2021

Related U.S. Application Data

(63) Continuation of application No. 15/456,892, filed on Mar. 13, 2017, now Pat. No. 10,850,056, which is a
(Continued)

(51) Int. Cl.
*A61M 16/00* (2006.01)
*A61M 16/08* (2006.01)

(52) U.S. Cl.
CPC ...... *A61M 16/024* (2017.08); *A61M 16/0003* (2014.02); *A61M 16/0051* (2013.01); *A61M 16/0057* (2013.01); *A61M 16/0063* (2014.02); *A61M 16/0833* (2014.02); *A61M 2016/0039* (2013.01); *A61M 2016/0042* (2013.01); *A61M 2205/502* (2013.01); *A61M 2205/505* (2013.01); *A61M 2230/202* (2013.01); *A61M 2230/40* (2013.01); *A61M 2230/42* (2013.01); *A61M 2230/432* (2013.01); *A61M 2230/46* (2013.01)

(58) Field of Classification Search
CPC .......... A61M 16/0003; A61M 16/0051; A61M 16/0063; A61M 16/024; A61M 16/026; A61M 2016/003; A61M 2016/0033; A61M 2016/0039; A61M 2016/0051; A61M 2230/40; A61M 2230/42; A61M 2230/46

See application file for complete search history.

(56) References Cited

U.S. PATENT DOCUMENTS

| | | |
|---|---|---|
| 3,444,857 A | 5/1969 | Godel |
| 3,481,333 A | 12/1969 | Garrison |

(Continued)

FOREIGN PATENT DOCUMENTS

| | | |
|---|---|---|
| EP | 0459647 | 12/1991 |
| EP | 0850652 | 7/1998 |

(Continued)

OTHER PUBLICATIONS

7200 Series Ventilator, Options, and Accessories: Operator's Manual. Nellcor Puritan Bennett, Part No. 22300 A, Sep. 1990.
(Continued)

*Primary Examiner* — Colin W Stuart
*Assistant Examiner* — Douglas Y Sul

(57) ABSTRACT

This disclosure describes systems and methods for controlling pressure and/or flow during exhalation. The disclosure describes novel exhalation modes for ventilating a patient.

20 Claims, 8 Drawing Sheets

Related U.S. Application Data continuation of application No. 13/098,130, filed on Apr. 29, 2011, now Pat. No. 9,629,971.

(56) References Cited

U.S. PATENT DOCUMENTS

| | | | |
|---|---|---|---|
| 3,485,243 A | 12/1969 | Bird | |
| 3,688,794 A | 9/1972 | Bird et al. | |
| 4,241,756 A | 12/1980 | Bennett et al. | |
| 4,406,291 A | 9/1983 | Schwesinger | |
| 4,527,557 A | 7/1985 | DeVries et al. | |
| 4,608,976 A | 9/1986 | Suchy | |
| 4,699,137 A | 10/1987 | Schroeder | |
| RE32,553 E | 12/1987 | Bennett et al. | |
| 4,712,580 A | 12/1987 | Gilman et al. | |
| 4,727,871 A | 3/1988 | Smargiassi et al. | |
| 4,747,403 A | 5/1988 | Gluck et al. | |
| 4,752,089 A | 6/1988 | Carter | |
| 4,921,642 A | 5/1990 | LaTorraca | |
| 4,954,799 A | 9/1990 | Kumar | |
| 4,957,107 A | 9/1990 | Sipin | |
| 4,991,576 A | 2/1991 | Henkin et al. | |
| 4,993,269 A | 2/1991 | Guillaume et al. | |
| 5,000,173 A | 3/1991 | Zalkin et al. | |
| 5,020,532 A | 6/1991 | Mahoney et al. | |
| 5,038,621 A | 8/1991 | Stupecky | |
| 5,057,822 A | 10/1991 | Hoffman | |
| 5,072,729 A | 12/1991 | DeVries | |
| 5,072,737 A | 12/1991 | Goulding | |
| 5,109,838 A | 5/1992 | Elam | |
| 5,127,400 A | 7/1992 | DeVries et al. | |
| 5,134,995 A | 8/1992 | Gruenke et al. | |
| 5,146,092 A | 9/1992 | Apperson et al. | |
| 5,150,291 A | 9/1992 | Cummings et al. | |
| 5,153,436 A | 10/1992 | Apperson et al. | |
| 5,161,525 A | 11/1992 | Kimm et al. | |
| 5,168,868 A | 12/1992 | Hicks | |
| 5,178,155 A | 1/1993 | Mault | |
| 5,237,987 A | 8/1993 | Anderson et al. | |
| 5,255,675 A | 10/1993 | Kolobow | |
| 5,259,373 A | 11/1993 | Gruenke et al. | |
| 5,269,293 A | 12/1993 | Löser et al. | |
| 5,271,389 A | 12/1993 | Isaza et al. | |
| 5,277,175 A | 1/1994 | Riggs et al. | |
| 5,279,549 A | 1/1994 | Ranford | |
| 5,299,568 A | 4/1994 | Forare et al. | |
| 5,301,667 A | 4/1994 | McGrail et al. | |
| 5,301,921 A | 4/1994 | Kumar | |
| 5,303,698 A | 4/1994 | Tobia et al. | |
| 5,303,699 A | 4/1994 | Bonassa et al. | |
| 5,309,901 A | 5/1994 | Beaussant | |
| 5,316,009 A | 5/1994 | Yamada et al. | |
| 5,319,540 A | 6/1994 | Isaza et al. | |
| 5,325,861 A | 7/1994 | Goulding | |
| 5,331,995 A | 7/1994 | Westfall et al. | |
| 5,333,606 A | 8/1994 | Schneider et al. | |
| 5,335,656 A | 8/1994 | Bowe et al. | |
| 5,339,807 A | 8/1994 | Carter | |
| 5,343,857 A | 9/1994 | Schneider et al. | |
| 5,343,858 A | 9/1994 | Winefordner et al. | |
| 5,351,522 A | 10/1994 | Lura | |
| 5,355,893 A | 10/1994 | Mick et al. | |
| 5,357,946 A | 10/1994 | Kee et al. | |
| 5,360,000 A | 11/1994 | Carter | |
| 5,368,019 A | 11/1994 | LaTorraca | |
| 5,368,021 A | 11/1994 | Beard et al. | |
| 5,369,277 A | 11/1994 | Knodle et al. | |
| 5,383,449 A | 1/1995 | Forare et al. | |
| 5,385,142 A | 1/1995 | Brady et al. | |
| 5,390,666 A | 2/1995 | Kimm et al. | |
| 5,398,677 A | 3/1995 | Smith | |
| 5,401,135 A | 3/1995 | Stoen et al. | |
| 5,402,796 A | 4/1995 | Packer et al. | |
| 5,407,174 A | 4/1995 | Kumar | |
| 5,413,110 A | 5/1995 | Cummings et al. | |
| 5,438,980 A | 8/1995 | Phillips | |
| 5,443,075 A | 8/1995 | Holscher | |
| 5,452,714 A | 9/1995 | Anderson et al. | |
| 5,467,766 A | 11/1995 | Ansite et al. | |
| 5,484,270 A | 1/1996 | Adahan | |
| 5,494,028 A | 2/1996 | DeVries et al. | |
| 5,497,767 A | 3/1996 | Olsson et al. | |
| 5,503,140 A | 4/1996 | Winefordner et al. | |
| 5,513,631 A | 5/1996 | McWilliams | |
| 5,517,983 A | 5/1996 | Deighan et al. | |
| 5,520,071 A | 5/1996 | Jones | |
| 5,524,615 A | 6/1996 | Power | |
| 5,531,221 A | 7/1996 | Power | |
| 5,540,220 A | 7/1996 | Gropper et al. | |
| 5,542,415 A | 8/1996 | Brady | |
| 5,542,416 A | 8/1996 | Chalvignac | |
| 5,544,674 A | 8/1996 | Kelly | |
| 5,546,935 A | 8/1996 | Champeau | |
| 5,549,106 A | 8/1996 | Gruenke et al. | |
| 5,568,910 A | 10/1996 | Koehler et al. | |
| 5,575,283 A | 11/1996 | Sjoestrand | |
| 5,596,984 A | 1/1997 | O'Mahoney et al. | |
| 5,598,838 A | 2/1997 | Servidio et al. | |
| 5,606,968 A | 3/1997 | Mang | |
| 5,616,923 A | 4/1997 | Rich et al. | |
| 5,617,847 A | 4/1997 | Howe | |
| 5,630,411 A | 5/1997 | Holscher | |
| 5,632,270 A | 5/1997 | O'Mahony et al. | |
| 5,645,048 A | 7/1997 | Brodsky et al. | |
| 5,657,750 A | 8/1997 | Colman et al. | |
| 5,660,171 A | 8/1997 | Kimm et al. | |
| 5,662,099 A | 9/1997 | Tobia et al. | |
| 5,664,560 A | 9/1997 | Merrick et al. | |
| 5,664,562 A | 9/1997 | Bourdon | |
| 5,671,767 A | 9/1997 | Kelly | |
| 5,672,041 A | 9/1997 | Ringdahl et al. | |
| 5,673,689 A | 10/1997 | Power | |
| 5,678,537 A | 10/1997 | Bathe et al. | |
| 5,683,232 A | 11/1997 | Adhan | |
| 5,692,497 A | 12/1997 | Schnitzer et al. | |
| 5,693,944 A | 12/1997 | Rich | |
| 5,694,926 A | 12/1997 | DeVries et al. | |
| 5,697,363 A | 12/1997 | Hart | |
| 5,701,883 A | 12/1997 | Hete et al. | |
| 5,701,889 A | 12/1997 | Danon | |
| 5,715,812 A | 2/1998 | Deighan et al. | |
| 5,762,480 A | 6/1998 | Adahan | |
| 5,771,884 A | 6/1998 | Yarnall et al. | |
| 5,789,660 A | 8/1998 | Kofoed et al. | |
| 5,791,339 A | 8/1998 | Winter | |
| 5,794,614 A | 8/1998 | Gruenke et al. | |
| 5,794,986 A | 8/1998 | Gansel et al. | |
| 5,797,393 A | 8/1998 | Kohl | |
| 5,803,064 A | 9/1998 | Phelps et al. | |
| 5,813,399 A | 9/1998 | Isaza et al. | |
| 5,823,179 A | 10/1998 | Grychowski et al. | |
| 5,826,575 A | 10/1998 | Lail | |
| 5,829,441 A | 11/1998 | Kidd et al. | |
| 5,845,636 A | 12/1998 | Gruenke et al. | |
| 5,857,458 A | 1/1999 | Tham et al. | |
| 5,864,938 A | 2/1999 | Gansel et al. | |
| 5,865,168 A | 2/1999 | Isaza | |
| 5,868,133 A | 2/1999 | DeVries et al. | |
| 5,875,783 A | 3/1999 | Kullik | |
| 5,876,352 A | 3/1999 | Weismann | |
| 5,881,717 A | 3/1999 | Isaza | |
| 5,881,722 A | 3/1999 | DeVries et al. | |
| 5,881,723 A | 3/1999 | Wallace et al. | |
| 5,884,623 A | 3/1999 | Winter | |
| 5,906,204 A | 5/1999 | Beran et al. | |
| 5,909,731 A | 6/1999 | O'Mahony et al. | |
| 5,915,379 A | 6/1999 | Wallace et al. | |
| 5,915,380 A | 6/1999 | Wallace et al. | |
| 5,915,382 A | 6/1999 | Power | |
| 5,918,597 A | 7/1999 | Jones et al. | |
| 5,921,238 A | 7/1999 | Bourdon | |
| 5,927,274 A | 7/1999 | Servidio et al. | |
| 5,931,160 A * | 8/1999 | Gilmore | A61M 16/0051 128/204.23 |
| 5,934,274 A | 8/1999 | Merrick et al. | |

(56) References Cited

U.S. PATENT DOCUMENTS

| | | |
|---|---|---|
| 5,937,854 A | 8/1999 | Stenzier |
| 5,937,856 A | 8/1999 | Jonasson et al. |
| 5,941,846 A | 8/1999 | Duffy et al. |
| 5,957,130 A | 9/1999 | Krahbichler et al. |
| 6,024,089 A | 2/2000 | Wallace et al. |
| 6,041,777 A | 3/2000 | Faithfull et al. |
| 6,041,780 A | 3/2000 | Richard et al. |
| 6,047,860 A | 4/2000 | Sanders |
| 6,068,602 A * | 5/2000 | Tham .................... A61B 5/085 600/533 |
| 6,073,630 A | 6/2000 | Adahan |
| 6,076,523 A | 6/2000 | Jones et al. |
| 6,095,139 A | 8/2000 | Psaros |
| 6,095,140 A | 8/2000 | Poon et al. |
| 6,099,481 A | 8/2000 | Daniels et al. |
| 6,102,038 A | 8/2000 | DeVries |
| 6,106,480 A | 8/2000 | Gama De Abreu et al. |
| 6,116,240 A | 9/2000 | Merrick et al. |
| 6,116,242 A | 9/2000 | Frye et al. |
| 6,116,464 A | 9/2000 | Sanders |
| 6,119,686 A | 9/2000 | Somerson et al. |
| 6,123,073 A | 9/2000 | Schlawin et al. |
| 6,123,074 A | 9/2000 | Hete et al. |
| 6,131,571 A | 10/2000 | Lampotang et al. |
| 6,135,106 A | 10/2000 | Dirks et al. |
| 6,135,967 A | 10/2000 | Fiorenza et al. |
| 6,142,150 A | 11/2000 | O'Mahony et al. |
| 6,148,814 A | 11/2000 | Clemmer et al. |
| 6,152,132 A | 11/2000 | Psaros |
| 6,152,135 A | 11/2000 | DeVries et al. |
| 6,155,986 A | 12/2000 | Brydon et al. |
| 6,158,432 A | 12/2000 | Biondi et al. |
| 6,161,539 A | 12/2000 | Winter |
| 6,176,234 B1 | 1/2001 | Salter et al. |
| 6,179,784 B1 | 1/2001 | Daniels et al. |
| 6,192,885 B1 | 2/2001 | Jalde |
| 6,196,222 B1 | 3/2001 | Heinonen et al. |
| 6,203,502 B1 | 3/2001 | Hilgendorf et al. |
| 6,217,524 B1 | 4/2001 | Orr et al. |
| 6,220,245 B1 | 4/2001 | Takabayashi et al. |
| 6,227,196 B1 | 5/2001 | Jaffe et al. |
| 6,269,812 B1 | 8/2001 | Wallace et al. |
| 6,273,444 B1 | 8/2001 | Power |
| 6,283,119 B1 | 9/2001 | Bourdon |
| 6,287,264 B1 | 9/2001 | Hoffman |
| 6,295,330 B1 | 9/2001 | Skog et al. |
| 6,295,985 B1 | 10/2001 | Kock et al. |
| 6,305,372 B1 | 10/2001 | Servidio |
| 6,305,373 B1 | 10/2001 | Wallace et al. |
| 6,306,098 B1 | 10/2001 | Orr et al. |
| 6,308,706 B1 | 10/2001 | Lammers et al. |
| 6,309,360 B1 | 10/2001 | Mault |
| 6,312,389 B1 | 11/2001 | Kofoed et al. |
| 6,321,748 B1 | 11/2001 | O'Mahoney |
| 6,325,785 B1 | 12/2001 | Babkes et al. |
| 6,325,978 B1 | 12/2001 | Labuda et al. |
| 6,349,922 B1 | 2/2002 | Rydin |
| 6,357,438 B1 | 3/2002 | Hansen |
| 6,358,215 B1 | 3/2002 | Ricciardelli |
| 6,360,745 B1 | 3/2002 | Wallace et al. |
| 6,369,838 B1 | 4/2002 | Wallace et al. |
| 6,371,113 B1 | 4/2002 | Tobia et al. |
| 6,390,091 B1 | 5/2002 | Banner et al. |
| 6,394,962 B1 | 5/2002 | Gama De Abreu et al. |
| 6,402,697 B1 | 6/2002 | Calkins et al. |
| 6,408,848 B1 | 6/2002 | Feldman et al. |
| 6,412,483 B1 | 7/2002 | Jones et al. |
| 6,415,788 B1 | 7/2002 | Clawson et al. |
| 6,419,634 B1 | 7/2002 | Gaston, IV et al. |
| 6,439,229 B1 | 8/2002 | Du et al. |
| 6,457,472 B1 | 10/2002 | Schwartz et al. |
| 6,463,930 B2 | 10/2002 | Biondi et al. |
| 6,467,478 B1 | 10/2002 | Merrick et al. |
| 6,471,658 B1 | 10/2002 | Daniels et al. |
| 6,484,719 B1 | 11/2002 | Berthon-Jones |
| 6,523,537 B1 | 2/2003 | Mas Marfany |
| 6,523,538 B1 | 2/2003 | Wikefeldt |
| 6,526,970 B2 | 3/2003 | DeVries et al. |
| 6,532,957 B2 | 3/2003 | Berthon-Jones |
| 6,532,960 B1 | 3/2003 | Yurko |
| 6,540,689 B1 | 4/2003 | Orr et al. |
| 6,543,449 B1 | 4/2003 | Woodring et al. |
| 6,546,930 B1 | 4/2003 | Emerson et al. |
| 6,550,479 B1 | 4/2003 | Duxbury |
| 6,553,991 B1 | 4/2003 | Isaza |
| 6,553,992 B1 | 4/2003 | Berthon-Jones et al. |
| 6,557,553 B1 | 5/2003 | Borrello |
| 6,557,554 B1 | 5/2003 | Sugiura |
| 6,564,798 B1 | 5/2003 | Jalde |
| 6,571,795 B2 | 6/2003 | Bourdon |
| 6,572,561 B2 | 6/2003 | Mault |
| 6,575,163 B1 | 6/2003 | Berthon-Jones |
| 6,575,164 B1 | 6/2003 | Jaffe et al. |
| 6,575,165 B1 | 6/2003 | Cook et al. |
| 6,575,918 B2 | 6/2003 | Kline |
| 6,584,973 B1 | 7/2003 | Biondi et al. |
| 6,606,994 B1 | 8/2003 | Clark |
| 6,616,615 B2 | 9/2003 | Mault |
| 6,616,896 B2 | 9/2003 | Labuda et al. |
| 6,619,289 B1 | 9/2003 | Mashak |
| 6,622,725 B1 | 9/2003 | Fisher et al. |
| 6,622,726 B1 | 9/2003 | Du |
| 6,629,934 B2 | 10/2003 | Mault et al. |
| 6,631,716 B1 | 10/2003 | Robinson et al. |
| 6,640,806 B2 | 11/2003 | Yurko |
| 6,644,310 B1 | 11/2003 | Delache et al. |
| 6,648,831 B2 | 11/2003 | Orr et al. |
| 6,648,832 B2 | 11/2003 | Orr et al. |
| 6,659,962 B2 | 12/2003 | Ricciardelli |
| 6,668,824 B1 | 12/2003 | Isaza et al. |
| 6,668,828 B1 | 12/2003 | Figley et al. |
| 6,668,829 B2 | 12/2003 | Biondi et al. |
| 6,675,801 B2 | 1/2004 | Wallace et al. |
| 6,688,307 B2 | 2/2004 | Berthon-Jones |
| 6,718,974 B1 | 4/2004 | Moberg |
| 6,725,447 B1 | 4/2004 | Gilman et al. |
| 6,729,331 B2 | 5/2004 | Kay |
| 6,739,334 B2 | 5/2004 | Valeij |
| 6,739,337 B2 | 5/2004 | Isaza |
| 6,755,193 B2 | 6/2004 | Berthon-Jones et al. |
| 6,761,167 B1 | 7/2004 | Nadjafizadeh et al. |
| 6,761,168 B1 | 7/2004 | Nadjafizadeh et al. |
| 6,763,829 B2 | 7/2004 | Jaffe et al. |
| 6,722,359 B2 | 8/2004 | Chalvignac |
| 6,723,055 B2 | 8/2004 | Hoffman |
| 6,772,762 B2 | 8/2004 | Piesinger |
| 6,805,121 B1 | 10/2004 | Flood et al. |
| 6,810,876 B2 | 11/2004 | Berthon-Jones |
| 6,814,074 B1 | 11/2004 | Nadjafizadeh et al. |
| 6,815,211 B1 | 11/2004 | Blazewicz et al. |
| 6,840,906 B2 | 1/2005 | Gama De Abreu et al. |
| 6,866,040 B1 | 3/2005 | Bourdon |
| 6,877,511 B2 | 4/2005 | DeVries et al. |
| 6,886,558 B2 | 5/2005 | Tanaka et al. |
| 6,896,713 B1 | 5/2005 | Eckerbom et al. |
| 6,908,438 B2 | 6/2005 | Orr et al. |
| 6,938,619 B1 | 9/2005 | Hickle |
| 6,954,702 B2 | 10/2005 | Pierry et al. |
| 6,955,651 B2 | 10/2005 | Kück et al. |
| 6,960,854 B2 | 11/2005 | Nadjafizadeh et al. |
| 6,968,840 B2 | 11/2005 | Smith et al. |
| 6,986,351 B2 | 1/2006 | Figley et al. |
| 6,990,980 B2 | 1/2006 | Richey et al. |
| 7,004,168 B2 | 2/2006 | Mace et al. |
| 7,017,574 B2 | 3/2006 | Biondi et al. |
| 7,018,340 B2 | 3/2006 | Jaffe et al. |
| 7,032,589 B2 | 4/2006 | Kerchanin, II et al. |
| 7,036,504 B2 | 5/2006 | Wallace et al. |
| 7,040,315 B1 | 5/2006 | Stromberg |
| 7,040,316 B2 | 5/2006 | Connelly et al. |
| 7,040,321 B2 | 5/2006 | Göbel |
| 7,043,979 B2 | 5/2006 | Smith et al. |
| 7,066,175 B2 | 6/2006 | Hamilton et al. |
| 7,066,177 B2 | 6/2006 | Pittaway et al. |

(56) References Cited

U.S. PATENT DOCUMENTS

| | | |
|---|---|---|
| 7,074,196 B2 | 7/2006 | Kück et al. |
| 7,077,131 B2 | 7/2006 | Hansen |
| RE39,225 E | 8/2006 | Isaza et al. |
| 7,117,438 B2 | 10/2006 | Wallace et al. |
| 7,118,537 B2 | 10/2006 | Baddour |
| 7,121,277 B2 | 10/2006 | Ström |
| 7,128,069 B2 | 10/2006 | Farrugia et al. |
| 7,135,001 B2 | 11/2006 | Orr et al. |
| 7,137,389 B2 | 11/2006 | Berthon-Jones |
| 7,152,604 B2 | 12/2006 | Hickle et al. |
| 7,168,597 B1 | 1/2007 | Jones et al. |
| 7,183,552 B2 | 2/2007 | Russell |
| 7,195,013 B2 | 3/2007 | Lurie |
| 7,210,478 B2 | 5/2007 | Banner et al. |
| 7,222,623 B2 | 5/2007 | DeVries et al. |
| 7,241,269 B2 | 7/2007 | McCawley et al. |
| 7,270,126 B2 | 9/2007 | Wallace et al. |
| 7,275,540 B2 | 10/2007 | Bolam |
| 7,291,115 B2 | 11/2007 | Cardona Burrul |
| 7,291,851 B2 | 11/2007 | DelFavero et al. |
| 7,302,949 B2 | 12/2007 | Pelerossi et al. |
| 7,320,321 B2 | 1/2008 | Pranger et al. |
| 7,334,578 B2 | 2/2008 | Biondi et al. |
| 7,335,164 B2 | 2/2008 | Mace et al. |
| 7,341,563 B2 | 3/2008 | Rich et al. |
| 7,347,205 B2 | 3/2008 | Levi |
| 7,347,825 B2 | 3/2008 | Vaughan et al. |
| 7,363,085 B1 | 4/2008 | Benser et al. |
| 7,367,337 B2 * | 5/2008 | Berthon-Jones .......................... A61M 16/0069 128/204.23 |
| 7,369,757 B2 | 5/2008 | Farbarik |
| 7,370,650 B2 | 5/2008 | Nadjafizadeh et al. |
| 7,392,806 B2 | 7/2008 | Yuen et al. |
| 7,421,296 B1 | 9/2008 | Benser et al. |
| 7,427,269 B2 | 9/2008 | George et al. |
| 7,428,902 B2 | 9/2008 | Du et al. |
| 7,432,508 B2 | 10/2008 | Daniels et al. |
| 7,460,959 B2 | 12/2008 | Jafari |
| 7,475,685 B2 | 1/2009 | Dietz et al. |
| 7,484,508 B2 | 2/2009 | Younes |
| 7,487,773 B2 | 2/2009 | Li |
| 7,487,778 B2 | 2/2009 | Freitag |
| 7,500,483 B2 | 3/2009 | Colman et al. |
| 7,509,957 B2 | 3/2009 | Duquette et al. |
| 7,519,425 B2 | 4/2009 | Benser et al. |
| 7,525,663 B2 | 4/2009 | Kwok et al. |
| 7,533,670 B1 | 5/2009 | Freitag et al. |
| 7,547,285 B2 | 6/2009 | Kline |
| 7,556,038 B2 | 7/2009 | Kirby et al. |
| 7,556,042 B2 | 7/2009 | West et al. |
| 7,562,657 B2 | 7/2009 | Blanch et al. |
| 7,588,033 B2 | 9/2009 | Wondka |
| 7,610,914 B2 | 11/2009 | Bolam et al. |
| 7,617,824 B2 | 11/2009 | Doyle |
| 7,621,271 B2 | 11/2009 | Brugnoli |
| 7,634,998 B1 | 12/2009 | Fenley |
| 7,644,713 B2 | 1/2010 | Berthon-Jones |
| 7,654,802 B2 | 2/2010 | Crawford, Jr. et al. |
| 7,668,579 B2 | 2/2010 | Lynn |
| 7,686,019 B2 | 3/2010 | Weiss et al. |
| 7,694,677 B2 | 4/2010 | Tang |
| 7,699,788 B2 | 4/2010 | Kuck et al. |
| 7,717,113 B2 | 5/2010 | Andrieux |
| 7,721,735 B2 | 5/2010 | Hamilton et al. |
| 7,721,736 B2 | 5/2010 | Urias et al. |
| D618,356 S | 6/2010 | Ross |
| 7,740,591 B1 | 6/2010 | Starr et al. |
| 7,753,052 B2 | 7/2010 | Tanaka |
| 7,779,840 B2 | 8/2010 | Acker et al. |
| 7,784,461 B2 | 8/2010 | Figueiredo et al. |
| 7,810,497 B2 | 10/2010 | Pittman et al. |
| 7,814,908 B2 | 10/2010 | Psaros |
| 7,819,815 B2 | 10/2010 | Younes |
| 7,823,588 B2 | 11/2010 | Hansen |
| 7,828,741 B2 | 11/2010 | Kline et al. |
| 7,846,739 B2 | 12/2010 | von Bahr et al. |
| 7,849,854 B2 | 12/2010 | DeVries et al. |
| 7,855,716 B2 | 12/2010 | McCreary et al. |
| 7,861,716 B2 | 1/2011 | Borrello |
| 7,870,857 B2 | 1/2011 | Dhuper et al. |
| D632,796 S | 2/2011 | Ross et al. |
| D632,797 S | 2/2011 | Ross et al. |
| 7,883,471 B2 | 2/2011 | Aljuri et al. |
| 7,885,771 B2 | 2/2011 | Roecker et al. |
| 7,891,354 B2 | 2/2011 | Farbarik |
| 7,893,560 B2 | 2/2011 | Carter |
| 7,900,626 B2 | 3/2011 | Daly |
| 7,913,690 B2 | 3/2011 | Fisher et al. |
| D638,852 S | 5/2011 | Skidmore et al. |
| 7,984,714 B2 | 7/2011 | Hausmann et al. |
| D643,535 S | 8/2011 | Ross et al. |
| 7,992,557 B2 | 8/2011 | Nadjafizadeh et al. |
| 8,001,967 B2 | 8/2011 | Wallace et al. |
| D645,158 S | 9/2011 | Sanchez et al. |
| 8,021,310 B2 | 9/2011 | Sanborn et al. |
| D649,157 S | 11/2011 | Skidmore et al. |
| D652,521 S | 1/2012 | Ross et al. |
| D652,936 S | 1/2012 | Ross et al. |
| D653,749 S | 2/2012 | Winter et al. |
| 8,113,062 B2 | 2/2012 | Graboi et al. |
| D655,405 S | 3/2012 | Winter et al. |
| D655,809 S | 3/2012 | Winter et al. |
| 8,181,648 B2 | 5/2012 | Perine et al. |
| 8,210,173 B2 | 7/2012 | Vandine |
| 8,210,174 B2 | 7/2012 | Farbarik |
| 8,240,684 B2 | 8/2012 | Ross et al. |
| 8,267,085 B2 | 9/2012 | Jafari et al. |
| 8,272,379 B2 | 9/2012 | Jafari et al. |
| 8,272,380 B2 | 9/2012 | Jafari et al. |
| 8,302,600 B2 | 11/2012 | Andrieux et al. |
| 8,302,602 B2 | 11/2012 | Andrieux et al. |
| 8,457,706 B2 | 6/2013 | Baker, Jr. |
| 8,792,949 B2 | 7/2014 | Baker, Jr. |
| 9,629,971 B2 * | 4/2017 | Masic ................ A61M 16/024 |
| 10,850,056 B2 * | 12/2020 | Masic ............... A61M 16/0051 |
| 2001/0029339 A1 | 10/2001 | Orr et al. |
| 2001/0031928 A1 | 10/2001 | Orr et al. |
| 2002/0026941 A1 | 3/2002 | Bondi et al. |
| 2002/0082512 A1 | 6/2002 | Strom |
| 2002/0128566 A1 | 9/2002 | Gama De Abreu et al. |
| 2002/0138213 A1 | 9/2002 | Mault |
| 2002/0148468 A1 | 10/2002 | Valeij |
| 2003/0047188 A1 | 3/2003 | Mace et al. |
| 2003/0062045 A1 | 4/2003 | Woodring et al. |
| 2003/0111078 A1 | 6/2003 | Habashi et al. |
| 2003/0140921 A1 | 7/2003 | Smith et al. |
| 2003/0191405 A1 | 10/2003 | Rich et al. |
| 2004/0003814 A1 | 1/2004 | Banner et al. |
| 2004/0050387 A1 | 3/2004 | Younes |
| 2004/0087867 A1 | 5/2004 | Gama De Abreu et al. |
| 2004/0138577 A1 | 7/2004 | Kline |
| 2004/0186391 A1 | 9/2004 | Pierry et al. |
| 2004/0256560 A1 | 12/2004 | Russell |
| 2004/0261793 A1 | 12/2004 | Stromberg et al. |
| 2005/0005936 A1 | 1/2005 | Wondka |
| 2005/0034726 A1 | 2/2005 | Pittaway et al. |
| 2005/0039748 A1 | 2/2005 | Andrieux |
| 2005/0098177 A1 | 5/2005 | Haj-Yahya et al. |
| 2005/0112325 A1 | 5/2005 | Hickle |
| 2005/0124907 A1 | 6/2005 | Kuck et al. |
| 2005/0139211 A1 | 6/2005 | Alston et al. |
| 2005/0139212 A1 | 6/2005 | Bourdon |
| 2005/0150494 A1 | 7/2005 | DeVries et al. |
| 2005/0217671 A1 | 10/2005 | Fisher et al. |
| 2005/0279358 A1 | 12/2005 | Richey et al. |
| 2005/0284476 A1 | 12/2005 | Blanche et al. |
| 2005/0285055 A1 | 12/2005 | DelFavero et al. |
| 2006/0009707 A1 | 1/2006 | Daniels et al. |
| 2006/0032499 A1 | 2/2006 | Halsnes |
| 2006/0052950 A1 | 3/2006 | Pierry et al. |
| 2006/0086357 A1 | 4/2006 | Soliman et al. |
| 2006/0129054 A1 | 6/2006 | Orr et al. |
| 2006/0130839 A1 | 6/2006 | Bassovich |

(56) References Cited

U.S. PATENT DOCUMENTS

| | | |
|---|---|---|
| 2006/0145078 A1 | 7/2006 | Russell |
| 2006/0201507 A1 | 9/2006 | Breen |
| 2006/0241508 A1 | 10/2006 | Jaffe et al. |
| 2006/0243278 A1 | 11/2006 | Hamilton et al. |
| 2006/0249148 A1 | 11/2006 | Younes |
| 2006/0249153 A1 | 11/2006 | DeVries et al. |
| 2006/0253038 A1 | 11/2006 | Kuck et al. |
| 2006/0278223 A1 | 12/2006 | Younes |
| 2007/0000494 A1 | 1/2007 | Banner et al. |
| 2007/0017515 A1 | 1/2007 | Wallace et al. |
| 2007/0028921 A1 | 2/2007 | Banner et al. |
| 2007/0062531 A1 | 2/2007 | Fisher et al. |
| 2007/0044798 A1 | 3/2007 | Levi |
| 2007/0068518 A1 | 3/2007 | Urias et al. |
| 2007/0068530 A1 | 3/2007 | Pacey |
| 2007/0073183 A1 | 3/2007 | Kline |
| 2007/0077200 A1 | 4/2007 | Baker |
| 2007/0095347 A1 | 5/2007 | Lampotang et al. |
| 2007/0107728 A1 | 5/2007 | Ricciardelli et al. |
| 2007/0113854 A1 | 5/2007 | Mcauliffe |
| 2007/0125377 A1 | 6/2007 | Heinonen et al. |
| 2007/0142716 A1 | 6/2007 | Biondi |
| 2007/0144521 A1 | 6/2007 | DeVries et al. |
| 2007/0144523 A1 | 6/2007 | Bolam et al. |
| 2007/0149891 A1 | 6/2007 | George et al. |
| 2007/0157930 A1 | 7/2007 | Soliman et al. |
| 2007/0157931 A1 | 7/2007 | Parker et al. |
| 2007/0163579 A1 | 7/2007 | Li et al. |
| 2007/0193579 A1 | 8/2007 | Duquette et al. |
| 2007/0199566 A1 | 8/2007 | Be'eri |
| 2007/0215154 A1 | 9/2007 | Borrello |
| 2007/0221221 A1 | 9/2007 | Cooke et al. |
| 2007/0225612 A1 | 9/2007 | Mace |
| 2007/0227537 A1 | 10/2007 | Bemister et al. |
| 2007/0232952 A1 | 10/2007 | Baddour |
| 2007/0240718 A1 | 10/2007 | Daly |
| 2007/0255160 A1 | 11/2007 | Daly |
| 2007/0272241 A1 | 11/2007 | Sanborn et al. |
| 2007/0272242 A1 | 11/2007 | Sanborn et al. |
| 2007/0273887 A1 | 11/2007 | Russell |
| 2007/0282214 A1 | 12/2007 | George et al. |
| 2007/0284361 A1 | 12/2007 | Nadjafizadeh et al. |
| 2008/0000471 A1 | 1/2008 | Bolam et al. |
| 2008/0009761 A1 | 1/2008 | Acker et al. |
| 2008/0011300 A1 | 1/2008 | Andreiux |
| 2008/0021339 A1 | 1/2008 | Gabriel et al. |
| 2008/0045825 A1 | 2/2008 | Melker et al. |
| 2008/0053438 A1 | 3/2008 | DeVries et al. |
| 2008/0053441 A1 | 3/2008 | Gottlib et al. |
| 2008/0058667 A1 | 3/2008 | Pierry et al. |
| 2008/0060646 A1 | 3/2008 | Isaza |
| 2008/0060656 A1 | 3/2008 | Isaza |
| 2008/0072896 A1 | 3/2008 | Setzer et al. |
| 2008/0072902 A1 | 3/2008 | Setzer et al. |
| 2008/0078390 A1 | 4/2008 | Milne et al. |
| 2008/0083644 A1 | 4/2008 | Janbakhsh et al. |
| 2008/0091117 A1 | 4/2008 | Choncholas et al. |
| 2008/0092894 A1 | 4/2008 | Nicolazzi et al. |
| 2008/0097234 A1 | 4/2008 | Nicolazzi et al. |
| 2008/0119753 A1 | 5/2008 | Ricciardelli et al. |
| 2008/0119754 A1 | 5/2008 | Hietala |
| 2008/0135044 A1 | 6/2008 | Freitag et al. |
| 2008/0168990 A1 | 7/2008 | Cooke et al. |
| 2008/0183094 A1 | 7/2008 | Schonfuss et al. |
| 2008/0196720 A1 | 8/2008 | Kollmeyer et al. |
| 2008/0202517 A1 | 8/2008 | Mitton et al. |
| 2008/0202518 A1 | 8/2008 | Mitton et al. |
| 2008/0202525 A1* | 8/2008 | Mitton ............... A61M 16/104 128/204.22 |
| 2008/0214947 A1 | 9/2008 | Hunt et al. |
| 2008/0230062 A1 | 9/2008 | Tham |
| 2008/0257349 A1 | 10/2008 | Hedner et al. |
| 2008/0276939 A1 | 11/2008 | Tiedje |
| 2009/0000621 A1 | 1/2009 | Haggblom et al. |
| 2009/0007914 A1 | 1/2009 | Bateman |
| 2009/0050153 A1 | 2/2009 | Brunner |
| 2009/0056708 A1 | 3/2009 | Stenzier et al. |
| 2009/0056719 A1 | 3/2009 | Newman |
| 2009/0071478 A1 | 3/2009 | Kalfon |
| 2009/0078251 A1 | 3/2009 | Zucchi et al. |
| 2009/0084381 A1 | 4/2009 | DeVries et al. |
| 2009/0090359 A1 | 4/2009 | Daviet et al. |
| 2009/0114223 A1 | 5/2009 | Bonassa |
| 2009/0133695 A1 | 5/2009 | Rao et al. |
| 2009/0137919 A1 | 5/2009 | Bar-Lavie et al. |
| 2009/0165795 A1 | 7/2009 | Nadjafizadeh et al. |
| 2009/0171176 A1 | 7/2009 | Andersohn |
| 2009/0188502 A1 | 7/2009 | Tiedje |
| 2009/0205661 A1 | 8/2009 | Stephenson et al. |
| 2009/0205663 A1 | 8/2009 | Vandine et al. |
| 2009/0217923 A1 | 9/2009 | Boehm et al. |
| 2009/0221926 A1 | 9/2009 | Younes |
| 2009/0229612 A1 | 9/2009 | Levi et al. |
| 2009/0235935 A1 | 9/2009 | Pacey |
| 2009/0241948 A1 | 10/2009 | Clancy et al. |
| 2009/0241951 A1 | 10/2009 | Jafari et al. |
| 2009/0241952 A1 | 10/2009 | Nicolazzi et al. |
| 2009/0241953 A1 | 10/2009 | Vandine et al. |
| 2009/0241955 A1 | 10/2009 | Jafari et al. |
| 2009/0241956 A1 | 10/2009 | Baker, Jr. et al. |
| 2009/0241957 A1 | 10/2009 | Baker, Jr. |
| 2009/0241958 A1 | 10/2009 | Baker, Jr. |
| 2009/0241962 A1 | 10/2009 | Jafari et al. |
| 2009/0241964 A1 | 10/2009 | Aljuri et al. |
| 2009/0247849 A1 | 10/2009 | McCutcheon et al. |
| 2009/0247853 A1 | 10/2009 | Debreczeny |
| 2009/0247891 A1 | 10/2009 | Wood |
| 2009/0250054 A1 | 10/2009 | Loncar et al. |
| 2009/0250059 A1 | 10/2009 | Allum et al. |
| 2009/0255533 A1 | 10/2009 | Freitag et al. |
| 2009/0260625 A1 | 10/2009 | Wondka |
| 2009/0263279 A1 | 10/2009 | Kline et al. |
| 2009/0270752 A1 | 10/2009 | Coifman |
| 2009/0277448 A1 | 11/2009 | Ahlemn et al. |
| 2009/0293877 A1 | 12/2009 | Blanch et al. |
| 2009/0299430 A1 | 12/2009 | Daviet et al. |
| 2009/0301486 A1 | 12/2009 | Masic |
| 2009/0301487 A1 | 12/2009 | Masic |
| 2009/0301490 A1 | 12/2009 | Masic |
| 2009/0301491 A1 | 12/2009 | Masic et al. |
| 2010/0011307 A1 | 1/2010 | Desfossez et al. |
| 2010/0012126 A1 | 1/2010 | Gandini |
| 2010/0024820 A1 | 2/2010 | Bourdon |
| 2010/0031961 A1 | 2/2010 | Schmidt |
| 2010/0051026 A1 | 3/2010 | Graboi |
| 2010/0051029 A1 | 3/2010 | Jafari et al. |
| 2010/0059058 A1 | 3/2010 | Kuo |
| 2010/0069761 A1 | 3/2010 | Karst et al. |
| 2010/0071689 A1 | 3/2010 | Thiessen |
| 2010/0071692 A1 | 3/2010 | Porges |
| 2010/0071695 A1 | 3/2010 | Thiessen |
| 2010/0071696 A1 | 3/2010 | Jafari |
| 2010/0071697 A1 | 3/2010 | Jafari et al. |
| 2010/0078017 A1 | 4/2010 | Andrieux et al. |
| 2010/0078026 A1 | 4/2010 | Andrieux et al. |
| 2010/0081119 A1 | 4/2010 | Jafari et al. |
| 2010/0081955 A1 | 4/2010 | Wood, Jr. et al. |
| 2010/0099999 A1 | 4/2010 | Hemnes et al. |
| 2010/0101577 A1 | 4/2010 | Kaestle et al. |
| 2010/0106037 A1 | 4/2010 | Kacmarek et al. |
| 2010/0125227 A1 | 5/2010 | Bird |
| 2010/0137733 A1 | 6/2010 | Wang et al. |
| 2010/0139660 A1 | 6/2010 | Adahan |
| 2010/0147302 A1 | 6/2010 | Selvarajan et al. |
| 2010/0147303 A1 | 6/2010 | Jafari et al. |
| 2010/0170512 A1 | 7/2010 | Kuypers et al. |
| 2010/0175695 A1 | 7/2010 | Jamison |
| 2010/0179392 A1 | 7/2010 | Chang et al. |
| 2010/0180897 A1 | 7/2010 | Malgouyres |
| 2010/0185112 A1 | 7/2010 | Van Kesteren et al. |
| 2010/0186744 A1 | 7/2010 | Andrieux |
| 2010/0198095 A1 | 8/2010 | Isler |
| 2010/0218765 A1 | 9/2010 | Jafari et al. |
| 2010/0218766 A1 | 9/2010 | Milne |

(56) References Cited

U.S. PATENT DOCUMENTS

| | | |
|---|---|---|
| 2010/0218767 A1 | 9/2010 | Jafari et al. |
| 2010/0222692 A1 | 9/2010 | McCawley et al. |
| 2010/0236553 A1 | 9/2010 | Jafari et al. |
| 2010/0236555 A1 | 9/2010 | Jafari et al. |
| 2010/0241019 A1 | 9/2010 | Varga et al. |
| 2010/0242961 A1 | 9/2010 | Mougel et al. |
| 2010/0249549 A1 | 9/2010 | Baker, Jr. et al. |
| 2010/0249584 A1 | 9/2010 | Albertelli |
| 2010/0252042 A1 | 10/2010 | Kapust et al. |
| 2010/0268106 A1 | 10/2010 | Johnson et al. |
| 2010/0268131 A1 | 10/2010 | Efthimion |
| 2010/0269834 A1 | 10/2010 | Freitag et al. |
| 2010/0282258 A1 | 11/2010 | Tailor et al. |
| 2010/0282259 A1 | 11/2010 | Figueiredo et al. |
| 2010/0286544 A1 | 11/2010 | Tanaka et al. |
| 2010/0288283 A1 | 11/2010 | Campbell et al. |
| 2010/0292601 A1 | 11/2010 | Dompeling et al. |
| 2010/0300446 A1 | 12/2010 | Nicolazzi et al. |
| 2010/0324437 A1 | 12/2010 | Freeman et al. |
| 2010/0324439 A1 | 12/2010 | Davenport |
| 2011/0004108 A1 | 1/2011 | Peyton |
| 2011/0009762 A1 | 1/2011 | Eichler et al. |
| 2011/0011400 A1 | 1/2011 | Gentner et al. |
| 2011/0023878 A1 | 2/2011 | Thiessen |
| 2011/0023879 A1 | 2/2011 | Vandine et al. |
| 2011/0023880 A1 | 2/2011 | Thiessen |
| 2011/0023881 A1 | 2/2011 | Thiessen |
| 2011/0029910 A1 | 2/2011 | Thiessen |
| 2011/0041849 A1 | 2/2011 | Chen et al. |
| 2011/0041850 A1 | 2/2011 | Vandie et al. |
| 2011/0066060 A1 | 3/2011 | von Bahr et al. |
| 2011/0126829 A1 | 6/2011 | Carter et al. |
| 2011/0126832 A1 | 6/2011 | Winter et al. |
| 2011/0126834 A1 | 6/2011 | Winter et al. |
| 2011/0126835 A1 | 6/2011 | Winter et al. |
| 2011/0126836 A1 | 6/2011 | Winter et al. |
| 2011/0126837 A1 | 6/2011 | Winter et al. |
| 2011/0128008 A1 | 6/2011 | Carter |
| 2011/0132361 A1 | 6/2011 | Sanchez |
| 2011/0132362 A1 | 6/2011 | Sanchez |
| 2011/0132364 A1 | 6/2011 | Ogilvie et al. |
| 2011/0132365 A1 | 6/2011 | Patel et al. |
| 2011/0132366 A1 | 6/2011 | Ogilvie et al. |
| 2011/0132367 A1 | 6/2011 | Patel |
| 2011/0132368 A1 | 6/2011 | Sanchez et al. |
| 2011/0132369 A1 | 6/2011 | Sanchez |
| 2011/0132371 A1 | 6/2011 | Sanchez et al. |
| 2011/0133936 A1 | 6/2011 | Sanchez et al. |
| 2011/0138308 A1 | 6/2011 | Palmer et al. |
| 2011/0138309 A1 | 6/2011 | Skidmore et al. |
| 2011/0138311 A1 | 6/2011 | Palmer |
| 2011/0138315 A1 | 6/2011 | Vandine et al. |
| 2011/0138323 A1 | 6/2011 | Skidmore et al. |
| 2011/0146681 A1 | 6/2011 | Jafari et al. |
| 2011/0146683 A1 | 6/2011 | Jafari et al. |
| 2011/0154241 A1 | 6/2011 | Skidmore et al. |
| 2011/0175728 A1 | 7/2011 | Baker, Jr. |
| 2011/0196251 A1 | 8/2011 | Jourdain et al. |
| 2011/0209702 A1 | 9/2011 | Vuong et al. |
| 2011/0209704 A1 | 9/2011 | Jafari et al. |
| 2011/0209707 A1 | 9/2011 | Terhark |
| 2011/0213215 A1 | 9/2011 | Doyle et al. |
| 2011/0259330 A1 | 10/2011 | Jafari et al. |
| 2011/0259332 A1 | 10/2011 | Sanchez et al. |
| 2011/0259333 A1 | 10/2011 | Sanchez et al. |
| 2011/0265024 A1 | 10/2011 | Leone et al. |
| 2011/0271960 A1 | 11/2011 | Milne et al. |
| 2011/0273299 A1 | 11/2011 | Milne et al. |
| 2012/0000467 A1 | 1/2012 | Milne et al. |
| 2012/0000468 A1 | 1/2012 | Milne et al. |
| 2012/0000469 A1 | 1/2012 | Milne et al. |
| 2012/0000470 A1 | 1/2012 | Milne et al. |
| 2012/0029317 A1 | 2/2012 | Doyle et al. |
| 2012/0030611 A1 | 2/2012 | Skidmore |
| 2012/0060841 A1 | 3/2012 | Crawford, Jr. et al. |
| 2012/0071729 A1 | 3/2012 | Doyle et al. |
| 2012/0090611 A1 | 4/2012 | Graboi et al. |
| 2012/0096381 A1 | 4/2012 | Milne et al. |
| 2012/0133519 A1 | 5/2012 | Milne et al. |
| 2012/0136222 A1 | 5/2012 | Doyle et al. |
| 2012/0137249 A1 | 5/2012 | Milne et al. |
| 2012/0137250 A1 | 5/2012 | Milne et al. |
| 2012/0167885 A1 | 7/2012 | Masic et al. |
| 2012/0185792 A1 | 7/2012 | Kimm et al. |
| 2012/0197578 A1 | 8/2012 | Vig et al. |
| 2012/0197580 A1 | 8/2012 | Vij et al. |
| 2012/0216809 A1 | 8/2012 | Milne et al. |
| 2012/0216810 A1 | 8/2012 | Jafari et al. |
| 2012/0216811 A1 | 8/2012 | Kimm et al. |
| 2012/0226444 A1 | 9/2012 | Milne et al. |
| 2012/0247471 A1 | 10/2012 | Masic et al. |
| 2012/0272960 A1 | 11/2012 | Milne |
| 2012/0272961 A1 | 11/2012 | Masic et al. |
| 2012/0272962 A1 | 11/2012 | Doyle et al. |
| 2017/0182269 A1 | 6/2017 | Masic |

FOREIGN PATENT DOCUMENTS

| | | |
|---|---|---|
| EP | 1205203 | 9/2004 |
| EP | 1189649 | 6/2005 |
| EP | 0965357 | 3/2007 |
| FR | 2695320 | 3/1994 |
| JP | 2002136595 | 5/2002 |
| WO | WO 199611717 | 4/1996 |
| WO | WO 9641571 | 12/1996 |
| WO | WO 9744636 | 11/1997 |
| WO | WO 2007/102866 | 9/2007 |
| WO | WO 2007109177 | 9/2007 |

OTHER PUBLICATIONS

7200 Ventilatory System: Addendum/Errata. Nellcor Puritan Bennett, Part No. 4-023576-00, Rev. A, Apr. 1988.

800 Operator's and Technical Reference Manual. Series Ventilator System, Nellcor Puritan Bennett, Part No. 4-070088-00, Rev. L, Aug. 2010.

840 Operator's and Technical Reference Manual. Ventilator System, Nellcor Puritan Bennett, Part No. 4-075609-00, Rev. G, Oct. 2006.

Cairo et al., "Mosby's Respiratory Care Equipment, Seventh Edition", Mosby, US, XP002524651, 2004, pp. 360-361 and 775-778.

Jaffe, Ph.D., Michael B., "Proximal Flow Measurement with the Series 3 Flow Sensors", Respironics, Inc., 2002, pp. 1-4.

PCT International Search Report, PCT/US2009/034363, dated Aug. 5, 2009.

PCT International Search Report, PCT/US2009/055889, dated Nov. 26, 2009.

PCT International Search Report, PCT/US2009/059102, dated Nov. 30, 2009.

Puritan Bennett 980 Series Ventilator Operator's Manual, Covidien, Jan. 29, 2014, Part. No. 10077893 A Jan. 2014, 506 pages.

\* cited by examiner

METHODS AND SYSTEMS FOR EXHALATION CONTROL AND TRAJECTORY OPTIMIZATION

CROSS-REFERENCE TO RELATED APPLICATIONS

This application is a continuation application of U.S. patent application Ser. No. 15/456,892, entitled "METHODS AND SYSTEMS FOR EXHALATION CONTROL AND TRAJECTORY OPTIMIZATION," filed on Mar. 13, 2017, which is a continuation application of U.S. patent application Ser. No. 13/098,130, entitled "METHODS AND SYSTEMS FOR EXHALATION CONTROL AND TRAJECTORY OPTIMIZATION," filed Apr. 29, 2011, the disclosures of which are hereby incorporated herein by reference.

INTRODUCTION

Medical ventilator systems have long been used to provide supplemental oxygen support to patients. These ventilators typically comprise a source of pressurized air and oxygen, and which is fluidly connected to the patient through a conduit or tubing. The amount of pressure in the gas mixture delivered to the patient may be controlled during ventilation including during inspiration and exhalation.

Patients on a ventilator system are more comfortable when the delivered volume of inspired gas is allowed to be exhaled in the shortest amount of time possible. Current exhalation modes are designed to reduce pressure in the tubing as fast as possible. Other exhalation modes reduce the pressure in the patient tubing to a preset positive end-expiratory pressure (PEEP) level as fast as possible and then maintain this PEEP level through the remainder of the exhalation period. These exhalation modes are based on the assumption that achieving the highest pressure gradient across the flow restriction promotes the greatest lung flow at any point in time, and the fastest rate of lung emptying.

SUMMARY

This disclosure describes systems and methods for controlling pressure and/or flow during exhalation. The disclosure describes novel exhalation modes for ventilating a patient.

In part, this disclosure describes a method for controlling exhalation during ventilation of a patient on a ventilator. The method includes:
  a) determining at least one determined pressure profile based on at least one received criterion for an exhalation by a patient being ventilated on a ventilator;
  b) selecting a pressure profile for delivery to the patient from the at least one determined pressure profile; and
  c) controlling at least one of airway pressure and flow based on the selected pressure profile during the exhalation by the patient.

Yet another aspect of this disclosure describes a method for optimizing a pressure profile delivered to a patient during exhalation on a ventilator including:
  a) delivering at least one of airway pressure and flow based on a pressure profile during a current exhalation to a patient during ventilation on a ventilator;
  b) monitoring at least one parameter during the current exhalation by the patient;
  c) modifying the pressure profile based at least in part on the monitored at least one parameter; and
  d) delivering at least one of a modified airway pressure and a modified flow based on the modified pressure profile to the patient during at least one of the current exhalation and the next exhalation.
Further, the modified pressure profile maintains a received PEEP.

The disclosure further describes a computer-readable medium having computer-executable instructions for performing a method controlling exhalation during ventilation of a patient on a ventilator. The method includes:
  a) repeatedly determining at least one determined pressure profile based on at least one received criterion for an exhalation by a patient being ventilated on a ventilator;
  b) repeatedly selecting a pressure profile for delivery to the patient from the at least one determined pressure profile; and
  c) repeatedly controlling at least one of airway pressure and flow based on the selected pressure profile during the exhalation by the patient.

The disclosure also describes a ventilator system including means for determining at least one determined pressure profile based on at least one received criterion for an exhalation by a patient being ventilated on a ventilator; means for selecting a pressure profile for delivery to the patient from the at least one determined pressure profile; and means for controlling at least one of airway pressure and flow based on the selected pressure profile during the exhalation by the patient.

The disclosure further describes a ventilator system including means for delivering at least one of airway pressure and flow based on a pressure profile during a current exhalation to a patient during ventilation on a ventilator; means for monitoring at least one parameter during the current exhalation by the patient; means for modifying the pressure profile based at least in part on the monitored at least one parameter; and means for delivering at least one of a modified airway pressure and a modified flow based on the modified pressure profile to the patient during at least one of the current exhalation and the next exhalation. Further, the modified pressure profile maintains a received PEEP.

These and various other features as well as advantages which characterize the systems and methods described herein will be apparent from a reading of the following detailed description and a review of the associated drawings. Additional features are set forth in the description which follows, and in part will be apparent from the description, or may be learned by practice of the technology. The benefits and features of the technology will be realized and attained by the structure particularly pointed out in the written description and claims hereof as well as the appended drawings.

It is to be understood that both the foregoing general description and the following detailed description are exemplary and explanatory and are intended to provide further explanation of the invention as claimed.

EXHALATION CONTROL AND TRAJECTORY OPTIMIZATION

The following drawing figures, which form a part of this application, are illustrative of embodiments, systems and methods described below and are not meant to limit the scope of the invention in any manner, which scope shall be based on the claims appended hereto.

Figure 7:
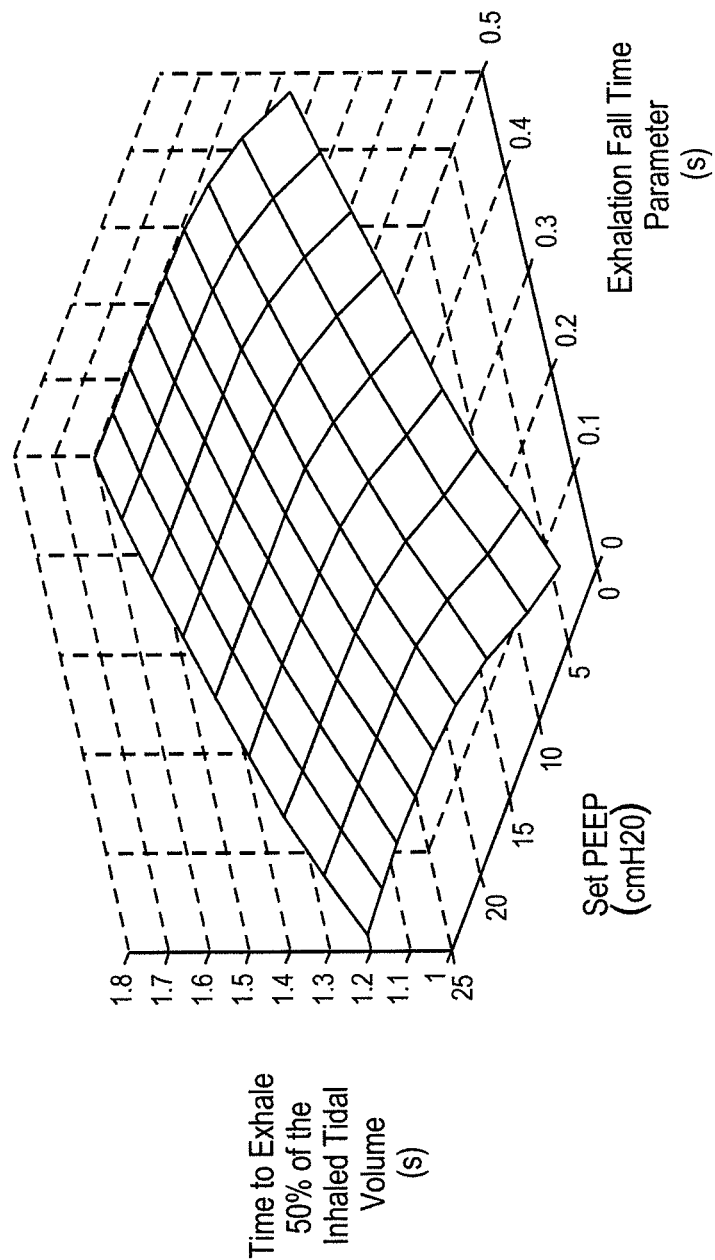
Figure 8:
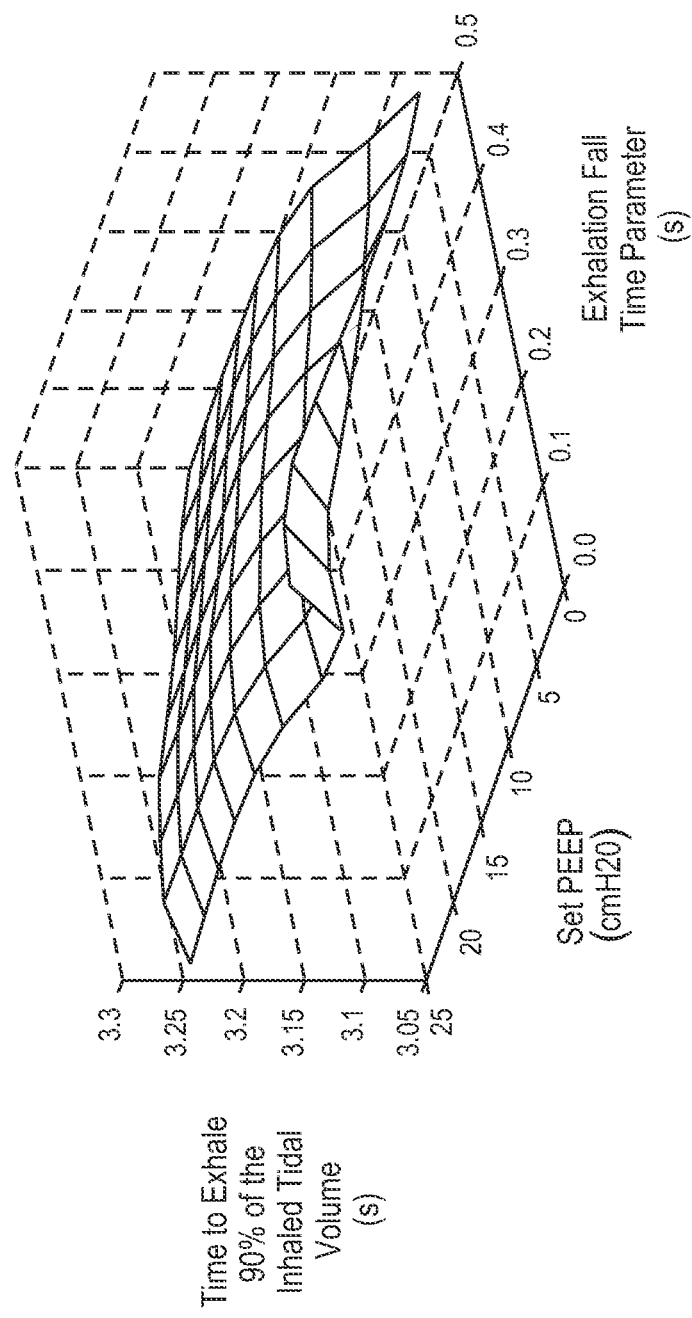

FIG. 7 illustrates an embodiment of a graph of the effect of different patient's tubing exhalation pressure profiles on the time required to passively exhale 50% of a given inspired tidal volume in simulations FIG. 8 illustrates an embodiment of a graph of the effect of different patient's tubing exhalation pressure profiles on the time required to passively exhale 90% of a given inspired tidal volume in simulations.

DETAILED DESCRIPTION

Although the techniques introduced above and discussed in detail below may be implemented for a variety of medical devices, the present disclosure will discuss the implementation of these techniques in the context of a medical ventilator for use in providing ventilation support to a human patient. The reader will understand that the technology described in the context of a medical ventilator for human patients could be adapted for use with other systems such as ventilators for non-human patients and general gas transport systems.

Medical ventilators are used to provide a breathing gas to a patient who may otherwise be unable to breathe sufficiently. In modern medical facilities, pressurized air and oxygen sources are often available from wall outlets. Accordingly, ventilators may provide pressure regulating valves (or regulators) connected to centralized sources of pressurized air and pressurized oxygen. The regulating valves function to regulate flow so that respiratory gas having a desired concentration of oxygen is supplied to the patient at desired pressures and rates. Ventilators capable of operating independently of external sources of pressurized air are also available.

While operating a ventilator, it is desirable to control the percentage of oxygen in the gas supplied by the ventilator to the patient. Further, it is desirable to control the amount of pressure delivered to the patient during inspiration. In some ventilators, it is desirable to control the amount of pressure delivered to the patient during exhalation.

The pressure control provided during exhalation is based on the assumption that patients find it more comfortable to exhale unimpeded. For example, modes of exhalation have been designed to reduce the pressure in the patient tubing to a preset positive end exhalation pressure (PEEP) level or to atmospheric pressure as fast as possible. If a preset PEEP is utilized, the exhalation mode must also maintain this pressure at the set PEEP level throughout exhalation. This exhalation approach is justified by the belief that achieving the highest pressure gradient across the flow restriction promotes the greatest lung flow at any point in time, and the fastest rate of lung emptying. This approach is correct if the resistance of the airways is independent from the actual pressure in the airways and lungs.

However, the resistance of lung airways may not always be independent from the actual pressure in the airways and lungs. It is suspected that a nonlinear character of resistance of internal lung airways causes the exhalation lung flow to decay more rapidly than normal thereby preventing complete lung emptying, causing patients discomfort, suboptimal ventilation, etc. For example, the physiology of the lung and airways associated with different disease states has been identified as a significant contributor to the impairment of the normal lung emptying process during exhalation. Thus, this nonlinear dependency of the airways resistance to the lung and airway pressure may result in a non-intuitive relationship between the optimum tubing pressure profile and the exhalation lung flow. Accordingly, it is desirable to modify the exhalation mode to obtain a faster rate of lung emptying or to decrease the amount of time it takes the patient to passively expire an inspired volume of gas to provide for faster and/or complete lung emptying.

Figure 1:
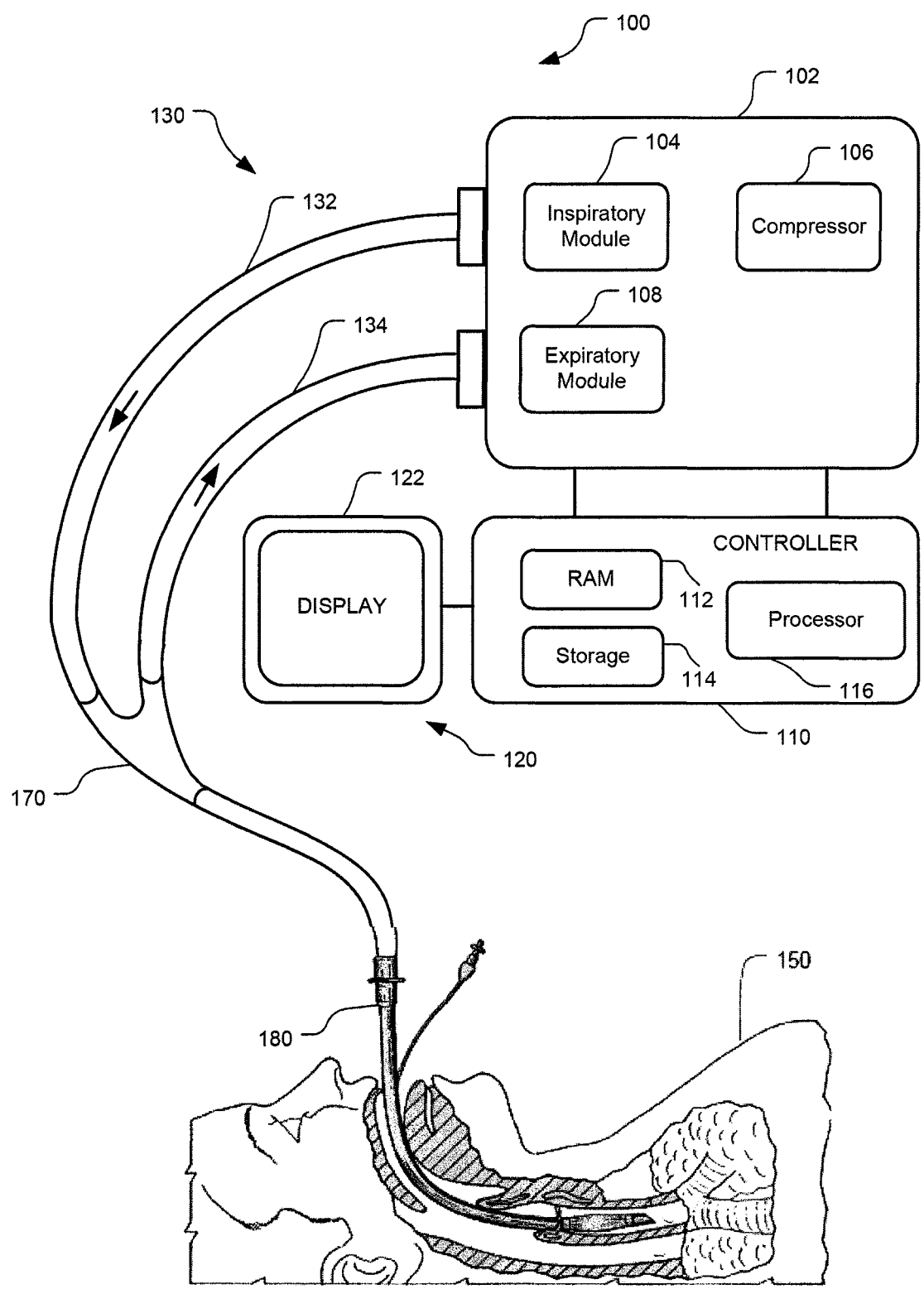
FIG. 1 illustrates an embodiment of a ventilator.

FIG. 1 is a diagram illustrating an embodiment of an exemplary ventilator 100 connected to a human patient 150. Ventilator 100 includes a pneumatic system 102 (also referred to as a pressure generating system 102) for circulating breathing gases to and from patient 150 via the ventilation tubing system 130, which couples the patient 150 to the pneumatic system 102 via an invasive (e.g., endotracheal tube, as shown) or a non-invasive (e.g., nasal mask) patient interface 180.

Ventilation tubing system 130 (or patient circuit 130) may be a two-limb (shown) or a one-limb circuit for carrying gases to and from the patient 150. In a two-limb embodiment, a fitting, typically referred to as a "wye-fitting" 170, may be provided to couple a patient interface 180 (as shown, an endotracheal tube) to an inspiratory limb 132 and an expiratory limb 134 of the ventilation tubing system 130.

Pneumatic system 102 may be configured in a variety of ways. In the present example, pneumatic system 102 includes an expiratory module 108 coupled with the expiratory limb 134 and an inspiratory module 104 coupled with the inspiratory limb 132. Compressor 106 or other source(s) of pressurized gases (e.g., air, oxygen, and/or helium) is coupled with inspiratory module 104 and the expiratory module 108 to provide a gas source for ventilatory support via inspiratory limb 132.

The inspiratory module 104 determines the pressure profiles delivered during inspiration. The expiratory module 108 determines the pressure profiles delivered during exhalation. In one embodiment, the inspiratory module 104 and the expiratory module 108 determine the pressure profiles during ventilation by controlling valves and gas flow within the ventilator 100. As used herein, the term "pressure profile" refers to how pressure is delivered for the entire period of exhalation, such as the amount of pressure per second or millisecond of the exhalation time period. In an alternative embodiment, the inspiratory module 104 and the expiratory module 108 determine the pressure profiles during ventilation by sending instructions to the controller 110 to control the valves and gas flow within the ventilator 100 during ventilation.

Previously utilized systems provided pressure control during exhalation based on the assumption that patients find it more comfortable to exhale fast and on the belief that achieving the highest pressure gradient across the flow restriction promotes the greatest lung flow at any point in time, and the fastest rate of lung emptying. This previously utilized approach is correct if the resistance of the airways is independent from the actual pressure in the airways and lungs. However, the resistance of lung airways may not always be independent from the actual pressure in the airways and lungs. It is suspected that a nonlinear character of resistance of internal lung airways causes the exhalation lung flow to decay more rapidly than normal thereby preventing complete lung emptying, causing patients discomfort, suboptimal ventilation, etc.

Accordingly, the expiratory module 108 determines the pressure profile delivered during exhalation based on at least one received criterion. The at least one received criterion does not include a received or set PEEP. However, the pressure profile determined by the expiratory module 108 may include a received or a set PEEP in addition to the received at least one criterion.

For the example, the at least one criterion may include a nonlinear relationship between airway resistance and the lung and airway pressure within a patient. A relationship between the airway resistance to lung and airway pressure exists because the lungs are essentially divided into two compartments: 1) the upper airways; and 2) the lower airways. These two compartments of the lung create a relationship, which is nonlinear, between airway resistance and lung and airway pressure. In one embodiment, this nonlinear relationship is modeled by the following equation:

$$R_L = f(P_{L1}, P_{L2}).$$

Figure 3:
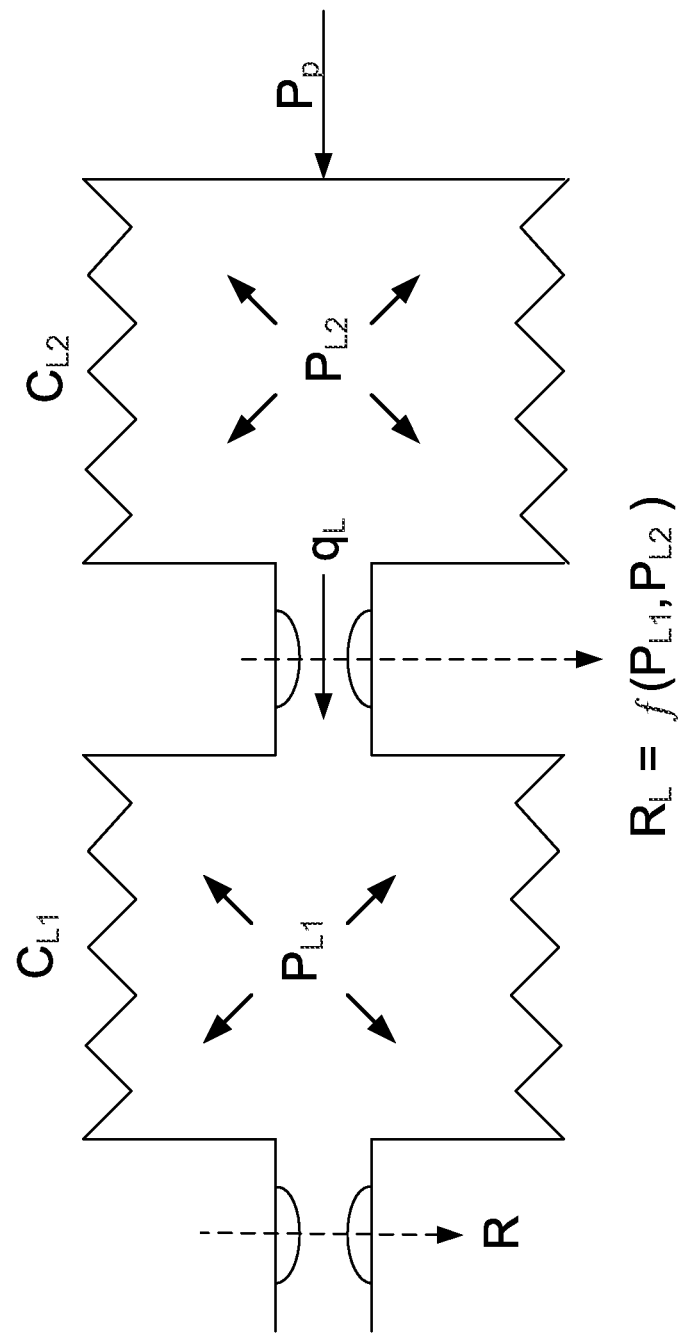
FIG. 3 illustrates an embodiment of a schematic model of a lung demonstrating the pressure and resistance relationship within the two compartments of the lung.

In the above equation $R_L$ is the amount of resistance in the lungs, $f(\bullet)$ is a nonlinear function of two values, $P_{L1}$ and $P_{L2}$, where, $P_{L1}$ is the amount of pressure in the first compartment of the lungs, and $P_{L2}$ is the amount of pressure in the second compartment of the lungs. As would be known by a person of skill in the art, the above nonlinear equation may be a function of more than two values. FIG. 3 illustrates this model by showing the pressure and resistance relationships between the upper airways or lung compartment 1 ($C_{L1}$), the lower airways or lung compartment 2 ($C_{L2}$), and the trachea. FIG. 3 also illustrates the flow ($q_L$) within the lungs and the external positive pressure ($P_p$) acting upon the lungs. Further, the physiology of the lung and airways associated with different disease states may be a significant contributor to the impairment of the normal lung emptying process. Accordingly, a pressure profile taking into account a nonlinear relationship, such as the example nonlinear relationship shown above, may provide for more comfortable and faster exhalation for some patients.

The nonlinear relationship of the lung illustrated above is just one example of a non-linear pressure flow relationship that may exist in a patient. Other nonlinear relationships, between airway resistance and lung and airway pressures may exist within a patient and vary between patients based on their measured parameters and diseases. For, example, the resistance can be a nonlinear function of more than two different local pressures measured in different parts of the lung and airways. Further, not all patients exhibit a measureable nonlinear relationship between airway resistance and lung and airway pressure. Accordingly, the expiratory module 108 determines the pressure profile to deliver during exhalation based on at least one received criterion, such as ventilator data, predetermined nonlinear pressure profiles, pressure profile trajectory equations, operator determined pressure profiles, and/or measured, derived, inputted, and/or selected patient parameters to determine how to provide a pressure profile with the fastest rate of lung emptying. As discussed above, the at least one criterion does not include a received/set PEEP. However, the at least one criterion may be any suitable criterion for controlling or effecting the pressure profile to provide for a faster rate of lung emptying, such as a percent of inspired volume/elapsed time, a flow as a function of delta P (estimated lung pressure and circuit pressure), an AutoPEEP, measurements of patient resistance and/or compliance, a diagnosis (e.g., chronic obstructive pulmonary disease), an inner diameter of artificial airway, a type of patient interface (e.g., mask or tube), an ideal body weight, carbon dioxide levels in exhaled gas and/or blood, an end expiratory flow, a patient assessment of comfort/dyspnea, a percentage of volume exhaled within a given period of time after the start of exhalation, a mean expiratory flow, a peak expiratory flow, a time to exhale a predetermined percentage of inspired volume, a time to reach a predetermined level of expiratory flow, a functional residual capacity (FRC), a ratio of functional residual capacity to total lung capacity (FRC/TLC), a breath rate, a ratio of inspiratory to expiratory time, a tidal volume, a forced expiratory volume in 1 second ($FEV_1$), an expiratory lung volume, and/or an instantaneous level of flow.

As used herein, any parameters/criteria that are "received" are input by the clinician, selected by the clinician, or provided by the ventilator. The ventilator may derive the "received" parameter/criteria based on patient parameters, ventilator parameters, and/or input or selected clinician data. In some embodiments, the ventilator contains stored default values that are "received" or utilized by the ventilator when the clinician does not input or select a parameter or a criterion. As used herein, the term "predetermined" designates that a value was set by a clinician and/or determined by the ventilator prior to use of the value.

The pneumatic system 102 may include a variety of other components, including mixing modules, valves, sensors, tubing, accumulators, filters, etc. Controller 110 is operatively coupled with pneumatic system 102, signal measurement and acquisition systems, and an operator interface 120 that may enable an operator to interact with the ventilator 100 (e.g., change ventilator settings, select operational modes, view monitored parameters, etc.). Controller 110 may include memory 112, one or more processors 116, storage 114, and/or other components of the type commonly found in command and control computing devices. In the depicted example, operator interface 120 includes a display 122 that may be touch-sensitive and/or voice-activated, enabling the display 122 to serve both as an input and output device.

The memory 112 includes non-transitory, computer-readable storage media that stores software that is executed by the processor 116 and which controls the operation of the ventilator 100. In an embodiment, the memory 112 includes one or more solid-state storage devices such as flash memory chips. In an alternative embodiment, the memory 112 may be mass storage connected to the processor 116 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 116. That is, computer-readable storage media includes non-transitory, volatile and non-volatile, removable and non-removable media implemented in any method or technology for storage of information such as computer-readable instructions, data structures, program modules or other data. For example, computer-readable storage media includes RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by the computer.

Figure 2:
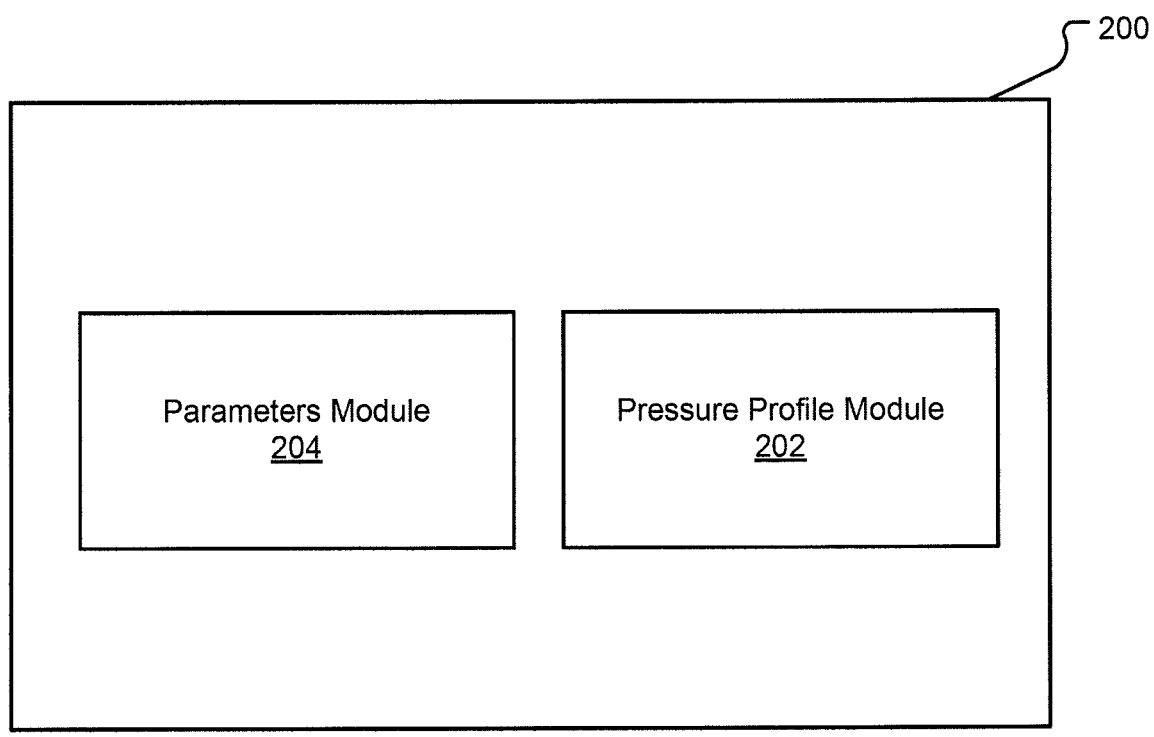
FIG. 2 illustrates an embodiment of an exhalation module.

FIG. 2 illustrates an exhalation module 200. The exhalation module 200 may include memory, one or more processors, storage, and/or other components of the type commonly found in command and control computing devices as described above. The exhalation module 200 further includes a pressure profile module 202 and a parameters module 204.

The pressure profile module 202 determines the pressure profile delivered during exhalation based on at least one received criterion. This pressure profile affects the amount of time a patient takes to exhale the inspired amount of inspiratory gas and rate of lung emptying.

The pressure profile module 202 utilizes at least one criterion for reducing the amount of time it takes the patient to exhale an inspired volume of gas and/or for increasing the rate of lung emptying as would be known by a person of skill in the art. As discussed above, the at least one criterion does not include a received PEEP. However, the pressure profile module 202 may utilize a received PEEP in addition to the received at least one criterion for determining the pressure profile. The at least one criterion may include ventilator data, predetermined pressure profiles, pressure profile trajectory equations, operator determined pressure profiles, a nonlinear relationship between airway resistance to the lung and airway pressure, and/or measured, derived, inputted, and/or selected patient parameters.

For example, the at least one criterion may include patient parameters, such as height, heart rate, weight, diseases, ideal body weight, etc. The criterion may further include ventilator data, such as flow rate, respiration rate, ventilation modes, expiration time, etc. The pressure profile module 202 may receive the at least one criteria from other ventilator components (e.g., a sensor, user interface, and/or controller) and/or may calculate/derive the desired criteria from received criteria or parameters. The ventilator may determine the desired pressure profile for each breath, over a fixed number of breaths (e.g., take data over a fixed number of breaths), or for a predetermined period of time. Further, the ventilator may repeat this calculation periodically as determined by a ventilator or as selected by the operator.

In some embodiments, the at least one criterion is ventilator data or patient parameters, such as a current ventilation mode and/or a diagnosed patient condition. In other embodiments, the criterion is a group of pressure profiles provided by the ventilator, which the operator may select the pressure profile from. Any suitable pressure profile for shortening the amount of time to exhale the delivered amount of inspiratory gas or for increasing the rate of lung emptying based on the at least one received criterion may be utilized by the exhalation module 200.

In one embodiment, the at least one criterion includes an exhalation pressure fall time parameter (EPFTP). The EPFTP is the amount of time it takes for the pressure to drop from the inspiratory pressure level to the set PEEP level during exhalation. In one embodiment, the actual rate of pressure decay in the ventilator is defined by the EPFTP. In another embodiment, the pressure profile module 202 determines the pressure profile based on the actual rate of pressure decay as defined by the EPFTP.

In a further embodiment, pressure profile module 202 determines the pressure profile based on the at least one criterion of an actual rate of pressure decay in the ventilator 100 as defined by predetermined parameters that are settable and modified by operators or the ventilator automatically. In another embodiment, the at least one criterion is a family of different pressure profiles that is utilized by the pressure profile module 202 to determine the pressure profile. The family of different pressure profiles may be defined by a predetermined set of criteria, such as EPFTP and exhalation time.

In an additional embodiment, the pressure profile module 202 utilizes at least one parameter that is repeatedly monitored during an exhalation to optimize the pressure profile. In this embodiment, the pressure profile is adjusted or modified during the current exhalation and/or before the next exhalation according to the monitored parameter in order to achieve a smaller time required to exhale the delivered amount of inspiratory gas and/or to achieve a faster rate of lung emptying in the next exhalation.

In another embodiment, the pressure profile module 202 utilizes repeated measurements of the time required to exhale the delivered amount of inspiratory gas to optimize the pressure profile. In this embodiment, different parameters of the pressure profile are adjusted after each exhalation according to the measured time required to exhale the delivered amount of inspiratory gas in order to achieve a shorter time required to exhale the delivered amount of inspiratory gas in the next exhalation.

In one embodiment, the at least one criterion is the pressure at the patient wye-fitting or the trajectory of the pressure profile. In some embodiments, the trajectory or the patient wye-fitting is determined based on the following equation:

$$P_y = PEEP + (EIP - PEEP)e^{-\alpha t}.$$

In this equation, $P_y$ is the pressure at the patient wye-fitting, PEEP is the set positive end exhalation pressure, EIP is the measured end inspiratory pressure, $\alpha$ is greater than zero and denotes the EPFTP, and t is the amount of time measured from the onset of an exhalation phase. This equation illustrates an exponential decay from EIP to PEEP, with alpha being varied to create different trajectories. For example, alpha may be varied (e.g., 0.1, 0.2, 0.3, . . . ∞) and then optimized based upon a predetermined parameter, such as the amount of time it takes the patient to exhale 50% of an inspired volume.

In some embodiments, the at least one criterion utilized by the pressure profile module is an operator-determined pressure profile. The operator may select or input a desired pressure profile or input various different parameters for modifying a pressure profile as desired. Allowing the operator to adjust, change, and input a pressure profile provides the operator with several benefits. For instance, the operator may select a pressure profile based on patient comfort. For example, the operator may deliver two different pressure profiles to a patient, ask the patient which profile the patient prefers, and then select a pressure profile based on the patient's answer.

Figure 4:
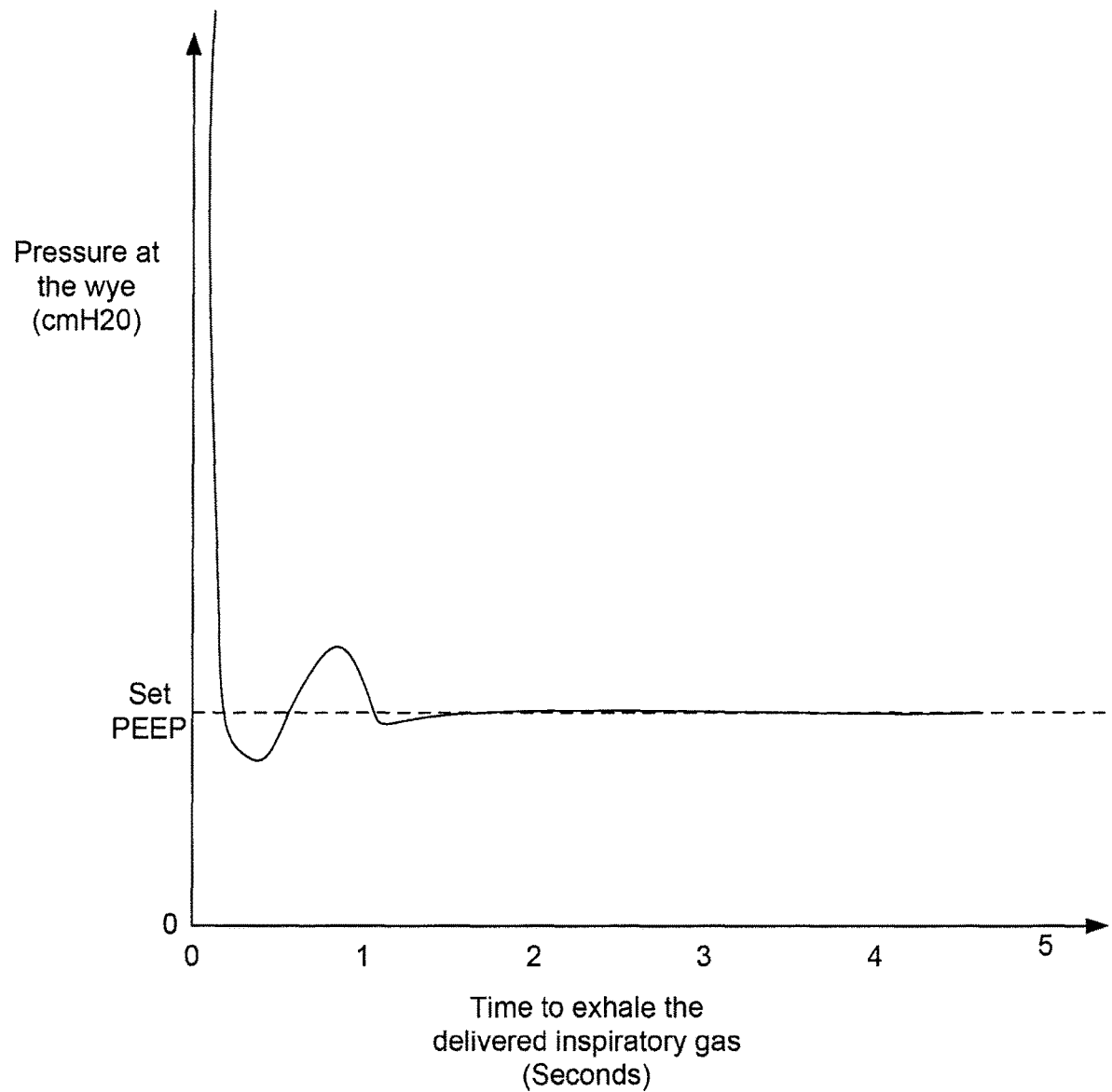
FIG. 4 illustrates an embodiment of a pressure profile.

In other embodiments, the at least one criterion utilized by the pressure profile module is a nonlinear relationship between airway resistance to the lung and airway pressure. In another embodiment, the pressure profile module 202 utilizes a predetermined nonlinear pressure profile as the at least one criteria, such as a nonlinear pressure profile with a fast initial decay in pressure followed by an increase of pressure to provide a shorter amount of time required to exhale the delivered amount of inspiratory gas. For example, an embodiment of a predetermined nonlinear pressure profile for the pressure profile module 202 is illustrated in FIG. 4. FIG. 4 illustrates a pressure profile with a fast initial decay of pressure that actually drops below a set PEEP, then increases in pressure to above the set PEEP at time 0.50 seconds followed by a gradual pressure reduction after the increase in pressure at time 0.8 seconds back down to the set PEEP.

The at least one criterion may be any suitable criterion for controlling or effecting the pressure profile to provide for a faster rate of lung emptying, such as a percent of inspired volume/elapsed time, a flow as a function of delta P (estimated lung pressure and circuit pressure), an AutoPEEP, measurements of patient resistance and/or compliance, a diagnosis (e.g., chronic obstructive pulmonary disease), an inner diameter of artificial airway, a type of patient interface (e.g., mask or tube), an ideal body weight, carbon dioxide levels in exhaled gas and/or blood, an end expiratory flow, a patient assessment of comfort/dyspnea, a percentage of volume exhaled within a given period of time after the start of exhalation, a mean expiratory flow, a peak expiratory flow, a time to exhale a predetermined percentage of inspired volume, a time to reach a predetermined level of expiratory flow, a functional residual capacity (FRC), a ratio of functional residual capacity to total lung capacity (FRC/TLC), a breath rate, a ratio of inspiratory to expiratory time, a tidal volume, a forced expiratory volume in 1 second ($FEV_1$), an expiratory lung volume, and/or an instantaneous level of flow.

The embodiments for determining the pressure profiles by the pressure profile module 202 as described and discussed above are exemplary only and may be utilized alone or in various combinations. It is understood by a person of skill in the art that any suitable pressure profile based on the received PEEP and the at least one received criterion may be utilized by the pressure profile module 202.

In some embodiments, if more than one pressure profile is determined by the pressure profile module 202, then the pressure profile module 202 selects the pressure profile with the fastest rate lung emptying to be sent to the parameters module 204. Further, the pressure profile module may present some or all of the unselected pressure profiles to the operator for selection depending on how the system is implemented and the degree of operator control desired. In a further embodiment, if more than one pressure profile is determined by the pressure profile module 202, then the pressure profile module 202 presents all of the pressure profiles to the operator for selection and continues to deliver the previously utilized pressure profile during exhalation until a new pressure profile is selected by the operator.

The ventilator may utilize various different methods to determine different pressure profiles. For example, the ventilator may utilize different criteria to determine different pressure profiles. In this embodiment, the ventilator may automatically select the pressure profile calculated with a specific criterion, such as a measurement of patient compliance and/or resistance, and only utilize the other calculated pressure profiles based on other criterion if a predetermined threshold is met by other measured patient or ventilator parameters. If the threshold is met, the ventilator may select a pressure profile calculated based on exhalation time. In some embodiments, the ventilator may have a predetermined nonlinear pressure profile stored, such as the one displayed in FIG. 4, in addition to a calculated pressure profile. In this embodiment, the ventilator may automatically select the calculated pressure profile unless a predetermined threshold is met by patient or ventilator measured parameters. For example, the predetermined threshold may be related to work of breathing or arterial blood gas saturation. The selection parameters listed above are merely exemplary. The ventilator may utilize any suitable means for selecting a pressure profile from a family of pressure profiles as would be known by a person of skill in the art for ventilating a patient.

In some embodiments, the family of pressure profiles is created utilizing the following equation:

$$P_y(t) = PEEP + (EIP - PEEP)e^{-\alpha t}$$

which is described in detail above. In this embodiment, different values for alpha ranging from 0.1 to 100 and/or to infinity may be applied over a time period to generate several different pressure profiles. The ventilator may select one of these calculated pressure profiles utilizing various different techniques. For example, the ventilator may compare the calculated pressure profiles to previously delivered pressure profiles and choose the calculated pressure profile closest to a previously utilized pressure profile that obtained the fastest rate of lung emptying. In another embodiment, the ventilator delivers a different calculated exhalation profile in each breath for at least two consecutive breaths. The ventilator in this scenario may then select which pressure profile to deliver based on a predetermined parameter, such as the amount of time it takes the patient to exhale 50% of an inspired volume, which was measured during the delivery of the pressure profile.

For example, a pressure profile with an alpha of 1 may be delivered in a first breath and a pressure profile with an alpha of 2 may delivered in a second breath. During the delivery of these pressure profiles the ventilator may measure the amount of time it takes a patient to exhale 90% of the volume of an inspired breath. In this example, the ventilator compares each of these measured times and then delivers in the next exhalation the pressure profile with the shortest measured time.

The parameters module 204 receives the pressure profile for the current or next exhalation from the pressure profile module 202. The parameters module 204 determines the necessary ventilator settings for delivering airway pressure and/or flow based on the received pressure profile. In one embodiment, the parameters module 204 sends the necessary ventilator settings to a controller for implementation. In an alternative embodiment, the parameters module 204 sends the instructions directly to the necessary component or components (e.g., to the exhalation valve) for implementing the desired pressure profile during exhalation.

In some embodiments, the exhalation module 200 is part of the pressure generating system 102, as illustrated in FIG. 1. In alternative embodiments, the exhalation module 200 is part of the controller 110. In some embodiments, the pressure profile module 202 and/or the parameters module 204 are separate from the exhalation module and are contained within the controller 110.

Figure 5:
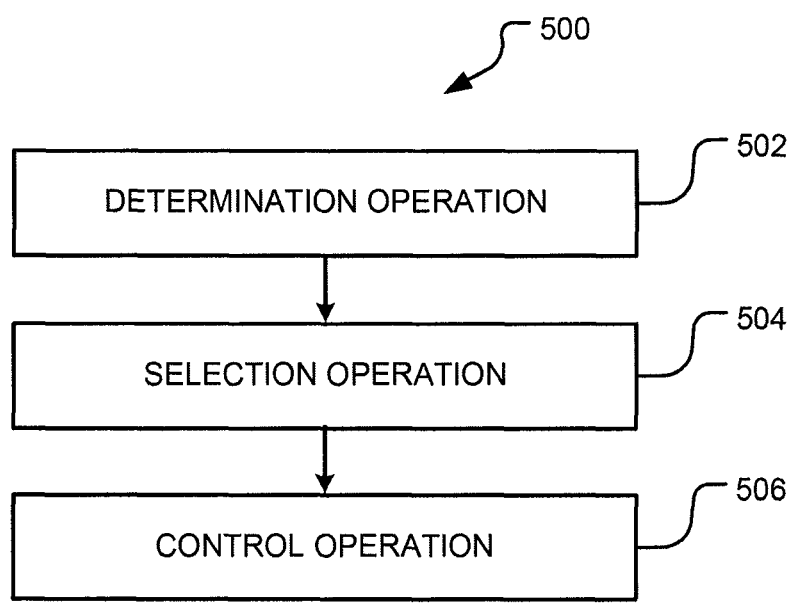
FIG. 5 illustrates an embodiment of a method for controlling exhalation during ventilation of a patient on a ventilator.

FIG. 5 illustrates an embodiment of a method 500 for controlling exhalation during ventilation of a patient on a ventilator. As illustrated, method 500 includes a determination operation 502. The ventilator in determination operation 502 determines at least one pressure profile by utilizing at least one received criterion for an exhalation by a patient being ventilated on a ventilator.

The at least one received criterion includes ventilation data, a nonlinear relationship between airway resistance and lung and airway pressure, predetermined pressure profiles, operator designed pressure profiles, pressure profile trajectory equations, and/or input, selected, measured, and/or derived patient parameters. As discussed above, the received criterion does not include a received PEEP. However, the determination operation 502 may utilize a received PEEP in addition to the received at least one criterion to determine the pressure profile. In some embodiments, the at least one criterion includes a current ventilation mode and/or a diagnosed patient condition. In some embodiments, the at least one criterion is a monitored parameter, such as a patient or ventilator parameter, from previous delivered exhalations. For example, the measured at least one parameter may be obtained for each breath, over a period of more than one breath (e.g., take data over a fixed number of breaths), or over a period of time. Any suitable pressure profile for shortening the amount of time to exhale the delivered amount of inspiratory gas and/or for increasing the rate of lung emptying may be utilized by the ventilator during method 500.

In one embodiment, the at least one criterion utilized by the ventilator in the determination operation 502 to determine the pressure profile is an EPFTP. In another embodiment, the at least one criterion utilized by the ventilator in the determination operation 502 to determine the pressure profile is the actual rate of pressure decay. The actual rate of pressure decay may be defined by the EPFTP. In a further embodiment, the at least one criterion utilized by the ventilator in the determination operation 502 to determine the pressure profile is the actual rate of pressure decay in the ventilator as defined by predetermined parameters, which are settable and modified by operators or the ventilator automatically. The parameters may be predetermined and may include the set PEEP and a measured end inspiratory pressure. In another embodiment, a family of different pressure profiles is utilized by the ventilator in the determination operation 502 to determine the pressure profile. The family of different pressure profiles is based on a set of received predetermined criteria, such as EPFTP and exhalation time. In an additional embodiment, the at least one received criterion utilized by the ventilator in the determination operation 502 is at least one parameter, such as a ventilation or patient parameter, that is repeatedly measured to optimize the pressure profile. For example, the ventilator in the determination operation 502 may repeatedly measure the time it takes the patient to exhale the delivered amount of inspiratory gas to optimize the pressure profile. The ventilator in the determination operation 502 may utilize any suitable means for determining the shortest time to expire the delivered amount of inspiratory gas and/or for determining the faster rate of lung emptying based on a received at least one criterion.

In some embodiments, the received at least one criterion is the pressure at the patient wye-fitting or the trajectory of the pressure profile. In one embodiment, the pressure at the patient wye-fitting or the trajectory of the pressure profile is determined by the ventilator in the determination operation 502 by utilizing the following equation:

$$P_y(t)=PEEP+(EIP-PEEP)e^{-\alpha t}.$$

In this equation, $P_y$ is the pressure at the patient wye-fitting, PEEP is the set positive end exhalation pressure, EIP is the measured end inspiratory pressure, $\alpha$ is greater than zero and denotes the EPFTP, and t is the amount of time measured from the onset of exhalation phase. This equation illustrates an exponential decay from EIP to PEEP, with alpha being varied to create different trajectories. For example, alpha may be varied (e.g., 0.1, 0.2, 0.3, ... $\infty$) and then optimized based upon a predetermined parameter, such as the amount of time it takes the patient to exhale 50% of an inspired volume.

In another embodiment, the at least one criterion utilized by the ventilator in the determination operation 502 to determine the pressure profile is a predetermined pressure profile. For example, the predetermined pressure profile may have a fast initial decay in pressure followed by an increase in pressure to provide a shorter amount of time required to exhale the delivered amount of inspiratory gas as illustrated in FIG. 4. In some embodiments, the determination operation 502 is performed by an exhalation module, a pressure profile module, pneumatic system, and/or a ventilator controller.

The at least one criterion may be any suitable criterion for controlling or effecting the pressure profile to provide for a faster rate of lung emptying, such as a percent of inspired volume/elapsed time, a flow as a function of delta P (estimated lung pressure and circuit pressure), an AutoPEEP, measurements of patient resistance and/or compliance, a diagnosis (e.g., chronic obstructive pulmonary disease), an inner diameter of artificial airway, a type of patient interface (e.g., mask or tube), an ideal body weight, carbon dioxide levels in exhaled gas and/or blood, an end expiratory flow, a patient assessment of comfort/dyspnea, a percentage of volume exhaled within a given period of time after the start of exhalation, a mean expiratory flow, a peak expiratory flow, a time to exhale a predetermined percentage of inspired volume, a time to reach a predetermined level of expiratory flow, a functional residual capacity (FRC), a ratio of functional residual capacity to total lung capacity (FRC/TLC), a breath rate, a ratio of inspiratory to expiratory time, a tidal volume, a forced expiratory volume in 1 second ($FEV_1$), an expiratory lung volume, and/or an instantaneous level of flow.

The embodiments as discussed above for determining the pressure profile in the determination operation 502 by the ventilator may be utilized alone or in various combinations.

Next, method 500 includes a selection operation 504. The ventilator in selection operation 504 selects a pressure profile from the at least one determined pressure profile. In one embodiment, the ventilator of method 500 selects the pressure profile predicted to provide the shortest amount of time to expire the delivered amount of inspiratory gas and/or to provide the fastest rate of lung emptying based the received at least one criterion. In an alternative embodiment, the operator selects a pressure profile from the at least one determined pressure profile.

As discussed above, the ventilator may utilize various different methods to determine different pressure profiles. For example, the ventilator may utilize different criteria to determine different pressure profiles for faster lung emptying. In this embodiment, the ventilator may automatically select the pressure profile calculated based on a specific predetermined criteria, such as such as a measurement of patient compliance and/or resistance, and only utilize the other calculated pressure profiles if a predetermined threshold is met by other measured patient or ventilator parameters. If the threshold is met in this embodiment, the ventilator may automatically select a pressure profile determined based on exhalation time. In some embodiments, the ventilator may have a stored predetermined nonlinear pressure profile, such as the one displayed in FIG. 4, in addition to a calculated pressure profile. In this embodiment, the ventilator may automatically select the calculated pressure profile unless a predetermined threshold is met by patient or ventilator measured parameters. For example, the predetermined threshold may be related to work of breathing or arterial blood gas saturation. The selection parameters listed above are merely exemplary. The ventilator may utilize any suitable means for selecting a pressure profile from a family of pressure profiles as would be known by a person of skill in the art for ventilating a patient.

In some embodiments, the family of pressure profiles is created utilizing the following equation:

$$P_y(t) = PEEP + (EIP - PEEP)e^{-\alpha t}$$

which is described in detail above. In this embodiment, different values for alpha ranging from 0.1 to 100 and/or to infinity may be applied over a time period to generate several different pressure profiles. The ventilator may select one of these calculated pressure profiles utilizing various different techniques. For example, the ventilator may compare the calculated pressure profiles to previously delivered pressure profiles and choose the calculated pressure profile closest to a previously utilized pressure profile that obtained the fastest rate of lung emptying. In another embodiment, the ventilator delivers a different calculated exhalation profile in each breath for at least two consecutive breaths. The ventilator in this scenario may then select which pressure profile to deliver based on a predetermined parameter, such as the amount of time it takes the patient to exhale 50% of an inspired volume, which was measured during the delivery of the pressure profile.

For example, a pressure profile with an alpha of 1 may be delivered in a first breath and a pressure profile with an alpha of 2 may be delivered in a second breath. During the delivery of these pressure profiles the ventilator may measure the amount of time it takes a patient to exhale 90% of the volume of an inspired breath. In this example, the ventilator compares each of these measured times and then delivers in the next exhalation the pressure profile that results in the shortest measured time.

Next, method 500 includes a control operation 506. The ventilator in control operation 506 controls airway pressure and/or flow based on the selected pressure profile during the exhalation by the patient. The ventilator in control operation 506 delivers the airway pressure and/or flow based on the selected pressure profile by modifying valve settings and/or flow rates during exhalation. In some embodiments, the control operation 506 is performed by an exhalation module, a parameters module, pneumatic system, and/or a ventilator controller.

Method 500 may also include an inspiration operation. In the inspiration operation, the ventilator delivers a volume of gas to the patient for inspiration during ventilation on the ventilator. The exhalation by the patient includes exhaling the volume of gas inhaled by the patient from the volume of delivered gas.

In one embodiment, method 500 is performed by the systems illustrated in FIGS. 1 and 2, which are described above.

In some embodiments, a microprocessor-based ventilator that accesses a computer-readable medium having computer-executable instructions for performing the method of controlling exhalation during ventilation of a patient is disclosed. This method includes repeatedly performing the steps disclosed in method 500 and as illustrated in FIG. 5.

In some embodiments, a ventilator system that includes: means for determining at least one determined pressure profile based on at least one received criterion for an exhalation by a patient being ventilated on a ventilator; means for selecting a pressure profile for delivery to the patient from the at least one determined pressure profile; and means for controlling airway pressure and/or flow based on the selected pressure profile during the exhalation by the patient.

Figure 6:
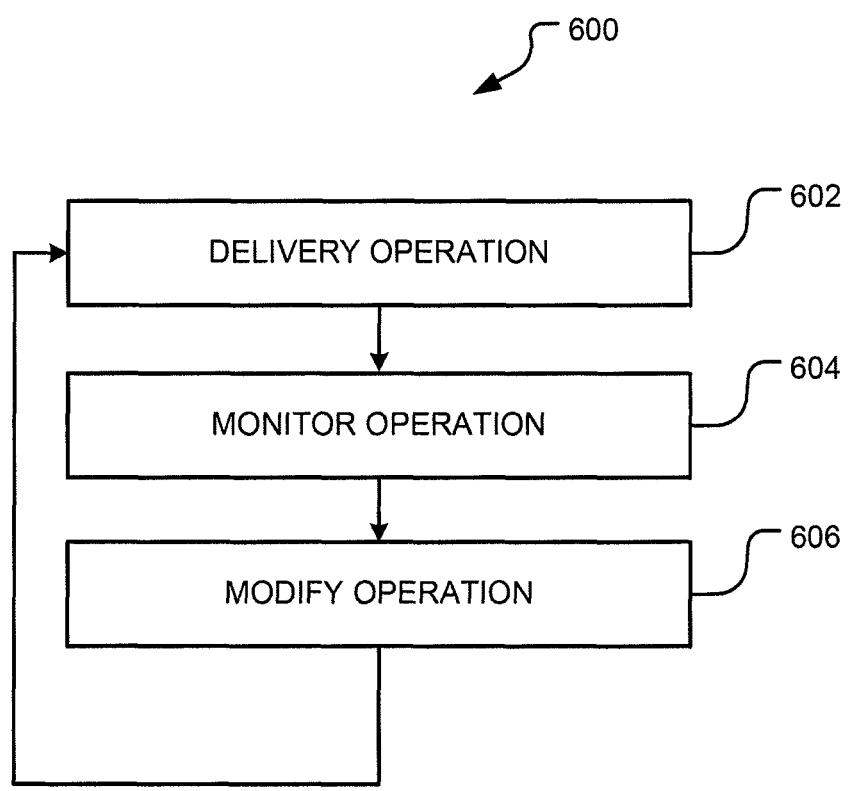
FIG. 6 illustrates an embodiment of a method for optimizing exhalation during ventilation of a patient on a ventilator.

FIG. 6 illustrates an embodiment of a method 600 for optimizing exhalation during ventilation of a patient on a ventilator. As illustrated, method 600 includes a delivery operation 602. The ventilator in delivery operation 602 delivers airway pressure and/or flow based on a pressure profile during an exhalation to a patient during ventilation on a ventilator. The pressure profile delivered during exhalation may be any suitable exhalation pressure profile. The ventilator either delivers pressure in accordance with a user-determined pressure profile or a ventilator-determined pressure profile. In some embodiments, the ventilator utilizes a nonlinear relationship between airway resistance to the lung and airway pressure to determine the pressure profile. In some embodiments, the ventilator utilizes a received at least one criterion to determine the pressure profile.

Next, method 600 includes a monitor operation 604. In the monitor operation 604, the ventilator monitors at least one parameter during the exhalation by the patient. The at least one parameter may be any suitable ventilator or patient parameter for determining a pressure profile for providing faster lung emptying. For example, the monitors at least one parameter may include ventilation data, data relating to a nonlinear relationship between airway resistance and lung and airway pressure, data relating to pressure profile trajectory equations, and/or measured/derived patient parameters. For example, the ventilator in the monitor operation 604 may monitor an exhalation time based on the amount of time it takes the patient to exhale at least a portion of gas inspired by the patient.

The monitor operation 604 may also include storing or calculating a pressure, flow and/or volume profile that describes the exhalation of the patient. Such a profile may be stored as a series of measured patient parameters taken during the exhalation phase. The ventilator may also or instead perform one or more mathematical analyses on the measured data in order to create a mathematical or model description of one or more parameter profiles during the exhalation phase.

Further, method 600 includes a modify operation 606. The ventilator in the modify operation 606 modifies the pressure profile based at least in part on the at least one monitored parameter in order to increase the rate of lung emptying and/or decrease the amount of time it takes the patient to exhale an inspired volume. Additionally, in order to increase the rate of lung emptying and/or to decrease exhalation time, the ventilator in the modify operation 606 may further adjust a number of other criteria, such as gas flow, ventilation modes, exhalation time, etc. However, the ventilator during the modify operation 606 does not adjust a received PEEP in the modified pressure profile. If a PEEP was received by the ventilator, the ventilator in the modify operation 606 maintains the received PEEP. For example, if the ventilator does not receive a PEEP, the ventilator during the modify operation 606 provides/determines a modified pressure profile with no PEEP. In some embodiments, the pressure profile is determined based on monitored parameters from a group of previously delivered exhalations. Any suitable pressure profile for shortening the amount of time to exhale the delivered amount of inspiratory gas or that increases the rate of lung emptying during exhalation may be utilized by the ventilator during method 600. For example, any suitable method for determining the pressure profile for method 600 as would be known by a person of skill in the art as described above in method 500 may be utilized by method 600.

Next, the ventilator during method 600 either continues with or repeats delivery operation 602. Again, the ventilator during delivery operation 602 delivers airway pressure and/or flow based on a pressure profile during an exhalation to a patient during ventilation on a ventilator. However, during this delivery operation 602, the ventilator delivers a modified airway pressure and/or a modified flow based on the modified pressure profile to the patient during the current and/or next exhalation. The current exhalation is the exhalation during which the received at least one parameter was monitored and utilized to calculate the modified pressure profile. The next exhalation is the exhalation subsequent to an exhalation where the received at least one parameter was monitored and utilized to calculate the modified pressure profile. The next exhalation may further include every exhalation, a predetermined number of exhalations, or the number of exhalations performed in a predetermined amount of time subsequent to the exhalation where the at least one criterion was monitored or subsequent to the current exhalation. Accordingly, the delivery of airway pressure and/or flow based on this modified pressure profile should reduce the amount of time required by the patient to exhale the delivered volume of gas inspired by the patient and/or should increase the rate of lung emptying during the current and/or next exhalation.

In some embodiments, the ventilator may repeat method 600 for every breath, after a predetermined number of breaths, or after a predetermined amount of time expires. In other embodiments, method 600 is performed by the systems illustrated in FIGS. 1 and 2, which are described above.

In some embodiments, a microprocessor-based ventilator that accesses a computer-readable medium having computer-executable instructions for performing the method of controlling exhalation during ventilation of a patient is disclosed. This method includes repeatedly performing the steps disclosed in method 600 and as illustrated in FIG. 6.

In other embodiments, a ventilator system that includes: means for delivering at least one of airway pressure and flow based on a pressure profile during a current exhalation to a patient during ventilation on a ventilator; means for monitoring at least one parameter during the current exhalation by the patient; means for modifying the pressure profile based at least in part on the monitored at least one parameter; and means for delivering at least one of a modified airway pressure and a modified flow based on the modified pressure profile to the patient during at least one of the current exhalation and the next exhalation. Further, the modified pressure profile maintains a received PEEP.

Example 1

During testing with various simulation tools, it was discovered that this nonlinear relationship between airway resistance of the internal lung with lung and airway pressure causes the exhalation lung flow to decay more rapidly than normal, thereby, preventing complete lung emptying when utilizing a pressure profile based on the assumption that achieving the highest pressure gradient across the flow restriction promotes the greatest lung flow at any point in time, and the fastest rate of lung emptying.

For example, during simulation, the time it takes for 50% of the inspired tidal volume to be exhaled by the patient increases as the exhalation pressure decay is reduced (or as the EPFTP increases) and target PEEP is increased, as illustrated by FIG. 7. FIG. 7 illustrates a graph of the effect of different patient's tubing exhalation pressure profiles on the time required to passively exhale 50% of a given inspired tidal volume in simulations.

For example, during simulation, the time it takes for 90% of the inspired tidal volume to be exhaled by the patient is reduced by reducing the rate of exhalation pressure decay (or increasing the EPFTP) and reducing the PEEP level, as illustrated in FIG. 8. FIG. 8 illustrates a graph of the effect of different patient's tubing exhalation pressure profiles on the time required to passively exhale 90% of a given inspired tidal volume in simulations. Further, FIG. 8 also illustrates that these changes affect the pressure profile performance non-monotonically.

Accordingly, these results show that decreasing pressure as fast as possible to the set PEEP rate does not always provide for the fastest exhalation. Further, these results show that a nonlinear relationship between airway resistance and lung and airway pressure exists within the lungs.

Those skilled in the art will recognize that the methods and systems of the present disclosure may be implemented in many manners and as such are not to be limited by the foregoing exemplary embodiments and examples. In other words, functional elements being performed by a single or multiple components, in various combinations of hardware and software or firmware, and individual functions, can be distributed among software applications at either the client or server level or both. In this regard, any number of the features of the different embodiments described herein may be combined into single or multiple embodiments, and alternate embodiments having fewer than or more than all of the features herein described are possible. Functionality may also be, in whole or in part, distributed among multiple components, in manners now known or to become known. Thus, myriad software/hardware/firmware combinations are possible in achieving the functions, features, interfaces and preferences described herein. Moreover, the scope of the present disclosure covers conventionally known manners for carrying out the described features and functions and interfaces, and those variations and modifications that may be made to the hardware or software or firmware components described herein as would be understood by those skilled in the art now and hereafter.

Numerous other changes may be made which will readily suggest themselves to those skilled in the art and which are encompassed in the spirit of the disclosure and as defined in the appended claims. While various embodiments have been described for purposes of this disclosure, various changes and modifications may be made which are well within the scope of the present invention. Numerous other changes may be made which will readily suggest themselves to those skilled in the art and which are encompassed in the spirit of the disclosure and as defined in the appended claims.

What is claimed is:

1. A method for controlling an exhalation phase during ventilation of a patient on a ventilator, the method comprising:
   determining, by a ventilator, a pressure profile for a future exhalation phase, the pressure profile causing a decrease in an exhalation time of the future exhalation phase relative to a previous exhalation phase of the patient;
   selecting the pressure profile for delivery to the patient; and
   based on the selected pressure profile, controlling, by the ventilator, at least one of airway pressure and flow during the future exhalation phase.

2. The method of claim 1, wherein determining the pressure profile is based on at least one criterion.

3. The method of claim 2, wherein the at least one criterion is a nonlinear relationship between airway resistance and lung pressure and the airway pressure.

4. The method of claim 2, wherein the at least one criterion is an exhalation pressure fall time parameter.

5. The method of claim 2, wherein the at least one criterion is an actual rate of pressure decay.

6. The method of claim 5, wherein the actual rate of pressure decay is defined by an exhalation pressure fall time parameter.

7. The method of claim 2, wherein the at least one criterion is an amount of time that the patient takes to exhale a delivered volume of gas inspired by the patient.

8. The method of claim 2, wherein the at least one criterion is a measured end inspiratory pressure.

9. The method of claim 2, wherein the at least one criterion is a trajectory for the pressure profile calculated with an equation of $p_y = PEEP + (EIP-PEEP)e^{-\alpha t}$, wherein the $\alpha$ is greater than zero and denotes an exhalation fall time parameter, wherein the PEEP is a set positive end-expiratory pressure (PEEP), wherein the EIP is a measured end expiratory pressure, wherein the t is an exhalation time, and wherein the $P_y$ is a pressure at a wye-fitting.

10. The method of claim 2, wherein the at least one criterion is a predetermined pressure profile that comprises:

allowing pressure to fall below a set PEEP by a predetermined amount;

increasing the pressure after the pressure falls below the set PEEP to another pressure above the set PEEP by a set amount; and subsequently allowing the another pressure above the set PEEP to fall to the set PEEP at a predetermined rate.

11. The method of claim 1, wherein the pressure profile for the exhalation is associated with complete lung emptying.

12. The method of claim 11, wherein determining the pressure profile is further based on a received PEEP.

13. The method of claim 12, further comprising:

delivering a volume of gas to the patient for inspiration during ventilation on the ventilator, wherein the exhalation by the patient includes exhaling at least 90% of the volume of gas delivered to the patient that was inspired by the patient.

14. A medical ventilator comprising:

a display;

a processor; and memory storing instructions that, when executed by the processor, cause the ventilator to perform a set of operations comprising:

delivering at least one of airway pressure and flow based on a pressure profile during a current exhalation to a patient during ventilation on the ventilator;

modifying the pressure profile for a future exhalation based on a non-linear relationship between an airway resistance, a lung pressure, and an airway pressure to form a modified pressure profile, wherein the modified pressure profile maintains a received PEEP; and based on the modified pressure profile, delivering at least one of a modified airway pressure and a modified flow to the patient during the future exhalation, wherein the modified pressure profile provides a decrease in an amount of time the patient takes to passively expire an inspired volume of gas for the future exhalation than a previous amount of time required by the patient to passively expire the inspired volume of gas during the current exhalation.

15. The medical ventilator of claim 14, the set of operations further comprising:

monitoring at least one parameter during the current exhalation by the patient, wherein the at least one parameter is at least one of:

a time to exhale a predetermined percentage of the inspired volume;

a percent of the inspired volume or the elapsed time; and a force expiratory volume in 1 second ($FEV_1$).

16. The medical ventilator of claim 15, wherein the modified pressure profile is further based on the at least one parameter.

17. The medical ventilator of claim 14, wherein the non-linear relationship is modeled based on a lung resistance equaling a nonlinear function between a first amount of a first pressure in an upper airways compartment of a lung and a second amount of a second pressure in a lower airways compartment of the lung.

18. The medical ventilator of claim 14, wherein a trajectory of the modified pressure profile is an exponential decay from EIP to PEEP.

19. The medical ventilator of claim 14, wherein the modified pressure profile further provides a decrease in an amount of time the patient takes to passively expire 90% of an inspired volume of gas than a previous amount of time required by the patient to passively expire 90% of the inspired volume of gas.

20. A medical ventilator comprising:

a display;

a processor; and memory storing instructions that, when executed by the processor, cause the ventilator to perform a set of operations comprising:

determining, with a ventilator, a pressure profile for a future exhalation phase, the pressure profile causing a decrease in an exhalation time of the future exhalation phase relative to a previous exhalation phase of a patient;

selecting the pressure profile for delivery to the patient; and based on the selected pressure profile, controlling, with the ventilator, at least one of airway pressure and flow during the future exhalation phase.

* * * * *